United States Patent [19]

Pearson

[11] Patent Number: 5,536,745

[45] Date of Patent: Jul. 16, 1996

[54] (HETERO)-ARYL KETONES DERIVATIVES WITH ANTIBACTERIAL PROPERTIES

[75] Inventor: Neil D. Pearson, Crawley, England

[73] Assignee: SmithKline Beecham p.l.c., London, England

[21] Appl. No.: 374,597

[22] PCT Filed: Jun. 24, 1993

[86] PCT No.: PCT/GB93/01331

§ 371 Date: Jan. 23, 1995

§ 102(e) Date: Jan. 23, 1995

[87] PCT Pub. No.: WO94/02478

PCT Pub. Date: Feb. 3, 1994

[30] Foreign Application Priority Data

Jul. 25, 1992 [GB] United Kingdom ............... 9215854

[51] Int. Cl.[6] ............... A61K 31/35; A61K 31/435; C07D 407/14; C07D 407/06

[52] U.S. Cl. ............... 514/460; 549/414; 549/415; 546/183; 514/299; 514/235.2

[58] Field of Search ............... 549/414; 514/460, 514/299, 235.2; 546/183; 544/127

[56] References Cited

FOREIGN PATENT DOCUMENTS

WO91/09855  7/1991  WIPO.
WO92/02518  2/1992  WIPO.

*Primary Examiner*—Johann Richter
*Assistant Examiner*—Laura R. Cross
*Attorney, Agent, or Firm*—Wayne J. Dustman; Stephen Venetianer; Edward T. Lentz

[57] ABSTRACT

Conformationally restricted aryl and heteroaryl ketones derived from monic acid have useful antibacterial properties.

5 Claims, No Drawings

(HETERO)-ARYL KETONES DERIVATIVES WITH ANTIBACTERIAL PROPERTIES

This application is a 371 of PCT/GB 93/01331 filed Jun. 24, 1993.

This invention relates to a novel class of compounds having antibacterial and antimycoplasmal activity, to processes for their preparation and to their use in human and veterinary medicine, and also to intermediates for use in the preparation of such compounds.

Mupirocin, the compound of formula (A):

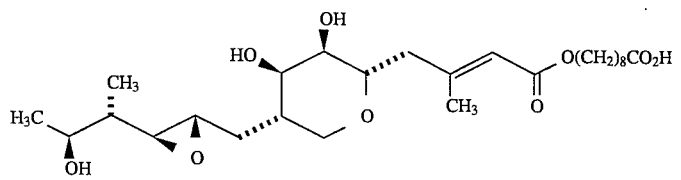

exhibits good activity against Gram positive bacteria. *H.infiuenzae*. Legionella and mycoplasma. It is marketed as a topical formulation by Beecham Group p.l.c. under the Trade Mark 'Bactroban'. Mupirocin (formerly known as pseudomonic acid A) is rapidly hydrolysed in vivo to monic acid A, the compound of formula (B):

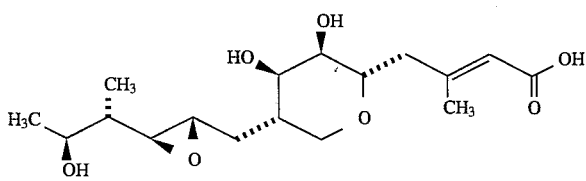

which is inactive.

Various proposals have been made in the past to improve the metabolic stability of mupirocin with respect to enzymatic hydrolysis, by modification of the C-1 ester functional group, for instance, by changing it to a C-1 heterocyclic derivative (EP-A-0 087 953 and EP-A-0 123 578. Beecham Group) or to a C-1 amide (EP-A-0 001 914. Beecham Group). In addition, EP-A-0029 665 (Beecham Group) discloses derivatives of monic acids A, B and C characterised in having a ketone functionality at C-1. including inter alia aryl and heterocyclic ketones. More recently, Klein et al have reported (in a poster presented at the Third Annual Chemical Congress of North America, Toronto, June 1988, some aspects of which are also discussed in J. Med. Chem. 1989, 32, 151) the preparation and properties of a limited group of C-1 aryl and heteroaryl ketones.

It has now been surprisingly found that enhanced antibacterial activity may be obtained if an element of conformational rigidity is introduced about the carbonyl moiety of a C-1 aryl or heteroaryl ketone. Improvements to in vitro activity and in vivo stability may be observed.

Accordingly, the present invention provides a compound of formula (I):

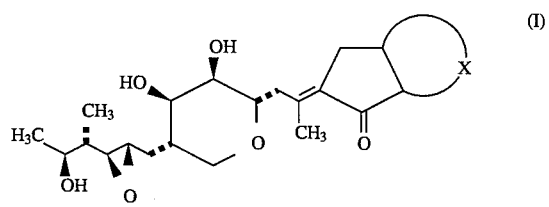

in which X denotes the residue of an aryl or a heteroaryl ring.

Suitably the aryl ring of which X forms a residue is benzene or naphthalene and preferably benzene, which may be unsubstituted or substituted by up to four, preferably up to two substituents.

Suitably the heteroaryl ring of which X forms a residue includes both single and fused rings, with each ring suitably comprising up to four heteroatoms each selected from oxygen, nitrogen and sulphur, which rings may be unsubstituted or substituted by, for example, up to three substituents. Each heteroaryl ring may have from 4 to 7, preferably 5 or 6, ring atoms. A fused heteroaryl ring may include an aryl ring and need include only one heteroaryl ring. Suitable fused heteroaryl rings include bicyclic systems. Preferably the heteroaryl ring of which X forms a residue is a monocyclic heteroaryl ring, for instance pyridine or furan.

In compounds of formula (I), preferred examples of the moiety:

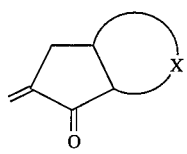

include

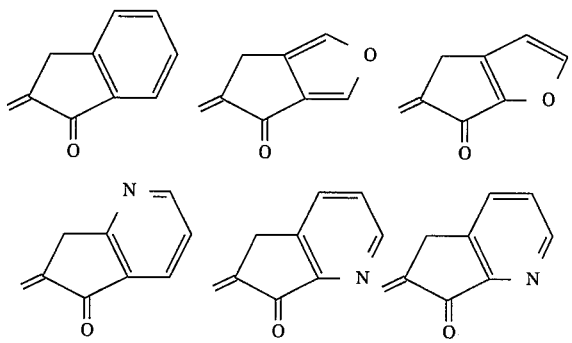

in each of which the aryl or heteroaryl ring may be optionally substituted. It will be appreciated that in these instances, the aryl ring of which X forms a residue is benzene and the heteroaryl ring of which X forms a residue is furan or pyridine.

Suitable substituents for the X residue (aryl or heteroaryl) ring, as defined above, include:

(a) halogen, cyano, azido, nitro, phthalimido, formyl, carboxy, carboxylate salts, sulpho, sulphonate salts, or oxo;

(b) amino, imino, hydrazino, hydrazono, ureido, guanidino, carbamoyl, or sulphonamido, in each of which groups a nitrogen may be further optionally substituted by one or two groups (which may be the same or different) selected from the groups listed in subparagraphs (d), (e) and (f);

(c) hydroxy, oxyimino, hydroxyimoyl, benzohydroxyimoyl, or mercapto, in each of which groups hydrogen may be replaced by one of the groups listed in subparagraphs (d), (e) and (f);

(d) a group Rp wherein Rp denotes an aryl, heteroaryl, or heterocyclyl moiety; each of which may be optionally substituted by up to three groups (the same or different) chosen from those groups listed in subparagraphs (a), (b), (c), (d), (e) and (f); and (e) a group $R^q$ wherein $R^q$ denotes $(C_{1-6})$alkyl, $(C_{3-7})$cycloalkyl, $(C_{2-6})$alkenyl, $(C_{3-8})$cycloalkenyl or $(C_{2-6})$alkynyl, each of which may be optionally substituted by up to three groups (which may be the same or different) chosen from the groups listed in subparagraphs (a), (b), (c), (d) and (f); and (f) groups $R^pCO-$, $R^pOCO-$, $R^qCO-$, $R^qOCO-$, $R^qSCO-$, $R^pSO-$, $R^pSO_2-$, $R^qSO-$, and $R^qSO_2-$ wherein $R^p$ and $R^q$ are as defined in subparagraphs (d) and (e) respectively.

Suitable substituents for an alkyl, cycloalkyl, alkenyl or alkynyl group as defined in group (e), include for example, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxy, $(C_{1-6})$alkoxy, acyloxy, oxo, acyl, 2-thenoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino, or iminoalkylamino.

Suitable substituents for an aryl group as defined in group (d) above, include for example, halogen, cyano, $(C_{1-6})$alkyl, phenyl, $(C_{1-6})$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$-alkoxy-carbonyl$(C_{1-6})$alkyl, $(C_{1-6})$alkylcarbonyloxy, $(C_{1-6})$alkylthio, $(C_{1-6})$alkylsulphinyl, $(C_{1-6})$alkylsulphonyl, sulphamoyl, mono- or di-$(C_{1-6})$alkylsulphamoyl, carbamoyl, and mono- or di-$(C_{1-6})$alkylcarbamoyl.

The aryl, heteroaryl, or heterocyclic substituent ring of group (d) may be substituted by another moiety of group (d) which may in turn be substituted by another group (a), (b), (c), (e) or (f), yielding for example a substituted bi-phenyl group.

Suitable substituents for a heteroaryl group as defined in group (d) above include, for example, halogen, $(C_{1-6})$alkyl, $(C_{1-6})$cycloalkyl, $(C_{1-6})$alkoxy, halo$(C_{1-6})$alkyl, hydroxy, amino, mono- or di-$(C_{1-6})$alkylamino, carboxy, $(C_{1-6})$alkoxycarbonyl, $(C_{1-6})$alkoxycarbonyl$(C_{1-6})$alkyl, aryl, oxo, non-aromatic heterocyclyl, $(C_{1-6})$alkylthio, $(C_{1-6})$alkylsulphinyl, or $(C_{1-6})$alkylsulphonyl.

Suitable substituents for a heterocyclic group as defined in group (d) above, include for example, halogen, $(C_{1-6})$alkyl, $(C_{1-6})$alkoxy, halo$(C_{1-6})$alkyl, hydroxy, amino, mono- or di-$(C_{1-6})$alkylamino, carboxy, $(C_{1-6})$alkoxycarbonyl, $(C_{1-6})$alkoxycarbonyl$(C_{1-6})$alkyl, aryl or oxo.

Preferred substituents for the X residue include hydroxy, $(C_{1-6})$alkoxy, $(C_{1-6})$alkylthio, $(C_{1-6})$alkylsulphinyl, $(C_{1-6})$alkylsulphonyl, di-$(C_{1-6})$alkylamino, N-morpholinyl, $(C_{1-6})$alkoxycarbonyl and carboxy.

When used herein, the term 'aryl' includes, unless otherwise defined, phenyl or naphthyl.

When used herein, the term 'heterocyclyl' includes aromatic and non-aromatic single or fused rings comprising up to four heteroatoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring. When used herein, the term 'halogen' refers to fluorine, chlorine, bromine or iodine.

When used herein, the term 'alkyl' refers to branched or straight hydrocarbon chains of 1 to 6 carbon atoms unless hereto defined otherwise, including but not limited to methyl, ethyl, isopropyl, n-propyl, and t-butyl.

When used herein, the term 'alkenyl' or 'alkynyl' refers to a branched or straight unsaturated hydrocarbon chain of 2 to 6 carbon atoms respectively unless hereto defined otherwise.

When used herein, the term 'cycloalkyl' refers to a cyclic hydrocarbon ring of 3 to 7 carbon atoms unless hereto defined otherwise, including but not limited to cyclopropyl, cyclopentyl and cyclohexyl.

It will be appreciated that compounds of formula (I) incorporate the 3-[(2S,3R,4R,5S)-5-[(2S,3S,4S,5S)-2.3-epoxy- 5-hydroxy-4-methylhexyl]-3,4-dihydroxytetrahydropyran- 2-yl]-2-methylprop-1(E)-enyl radical, as shown in formula (II):

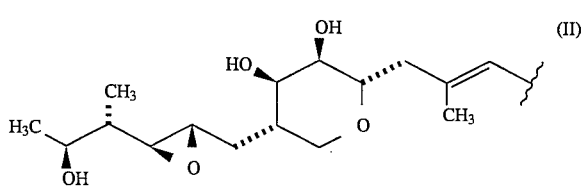

which radical is present in mupirocin.

It will be appreciated that in compounds of formula (I), substituents of the group X may contain one or more chiral centres. The present invention encompasses all such resultant isomeric possibilities.

Compounds of formula (I) may be prepared by a process which comprises treating a compound of formula (III):

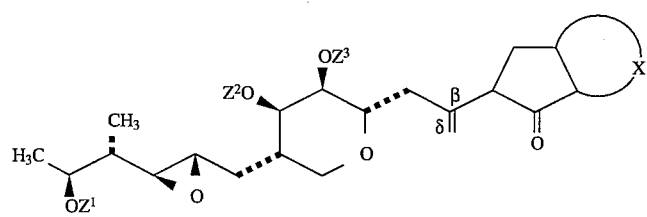

in which $Z^1$, $Z^2$ and $Z^3$ may be the same or different and is each a hydroxyl protecting group, with a reagent to effect conjugation of the β,δ double bond of the compound of formula (III) with the carbonyl group, and, thereafter, removing the hydroxyl protecting groups $Z^1$, $Z^2$ and $Z^3$.

Suitable reagents for effecting said conjugation include such as metal alkoxides, for instance potassium t-butoxide, organic bases such as DBU (1,8-diazabicyclo[5.4.0]undec-7-ene) and DBN (1,5-diazabicyclo [4.3.0]-non-5-ene). The reaction is preferably carried out at a low temperature, for instance at between about −90° C. and about −70° C., in a polar solvent such as tetrahydrofuran or an ether such as 1,2-dimethoxyethane or di-iso-propylether.

Compounds of formula (III) are novel and useful as intermediates in the preparation of compounds of formula (I).

Accordingly, in a further aspect, the present invention provides compounds of formula (III), as hereinbefore defined.

Compounds of formula (III) may be obtained by a process which comprises treating a compound of formula (IV):

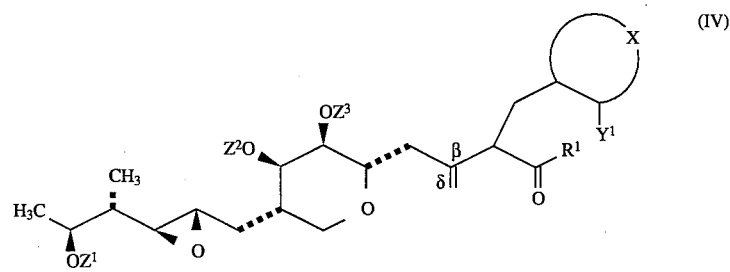

in which:

$R^1$ is a group $-N(OR^2)R^3$, $NR^4R^5$ or $OR^6$, in which $R^2$ and $R^3$ are the same or different and each is $(C_{1-6})$alkyl or the substituents $R^2$ and $R^3$ together form a $(C_{2-7})$alkylene chain;

$R^4$ and $R^5$ are the same or different and each is $(C_{1-6})$alkyl or the substituents $R^4$ and $R^5$ together form a $(C_{2-7})$alkylene chain or $R^4$ and $R^5$, together with the nitrogen atom to which they are bonded, form an imidazolyl or triazolyl ring;

$R^6$ is $(C_{1-10})$alkyl, optionally substituted with $(C_{1-6})$ alkylcarboxy, $Y^1$ is bromine or iodine; and X, $Z^1$, $Z^2$ and $Z^3$ are as hereinbefore defined, with a metallating agent, to effect metal-halogen ($Y^1$) exchange and thereby initiate intramolecular cyclisation.

Suitable metallating agents include organometallic reagents such as, for instance, organolithium reagents such as t-butyl lithium or n-butyl lithium. Preferably the reaction is carried out at a temperature in the range from about −30° C. to about 70° C., and in a suitable solvent conventionally used in such lithiation reactions, such as for instance tetrahydrofuran diisopropylene or 1,2-dimethoxyethane.

Compounds of formula (IV) are novel compounds and useful as intermediates in the preparation of compounds of formula (I). Accordingly, in a further aspect, the present invention provides a compound of formula (IV) as hereinbefore defined.

Preferably, in the compound of formula (IV), $R^1$ is $N(OR^2)R^3$ in which $R^2$ and $R^3$ is each methyl.

In an alternative process, a compound of formula (I), as hereinbefore defined, may be prepared by a process which comprises treating a compound of formula (V):

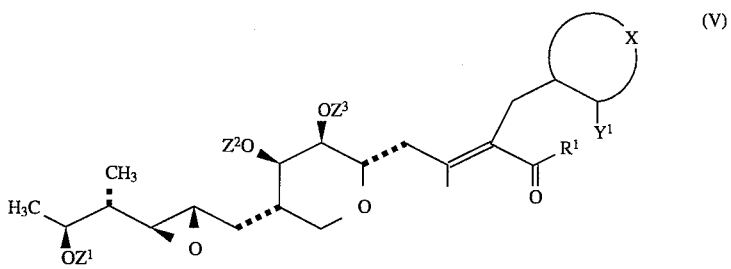
(V)

in which $Y^1$, $Z^1$, $Z^2$ and $Z^3$ are as hereinbefore defined, with a metallating agent, to effect metal-halogen ($Y^1$) exchange and thereby initiate intramolecular cyclisation, as hereinbefore defined, and thereafter removing the hydroxyl protecting groups $Z^1$, $Z^2$ and $Z^3$.

Compounds of formula (V) are novel and useful as intermediates in the preparation of compounds of formula (I). Accordingly, in a further aspect, the present invention provides compounds of formula (V), as hereinbefore defined.

Compounds of formula (V), as hereinbefore defined, may be obtained from compounds of formula (IV), as hereinbefore defined, by treatment thereof with a reagent to effect conjugation of the β, δ-double bond of the compound of formula (IV) with the carbonyl group, using a suitable metal alkoxide or organic base, as hereinbefore described.

It will be appreciated that in some instances and depending upon the particular choice of reagent, the reagent used to effect intramolecular cyclisation may also cause, to a lesser or greater degree, double bond conjugation and vice versa.

In such circumstances, it may be found more convenient to carry through the reaction product mixture of the first cyclisation or conjugation step through to the second conjugation or cyclisation step (respectively), rather than attempt separation at the intermediate step.

A compound of formula (IV) may be obtained by a process which comprises treating a compound of formula (VI):

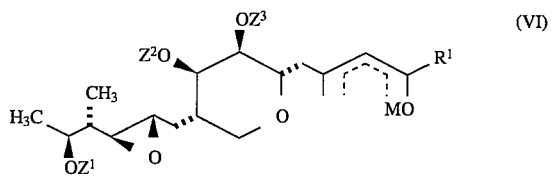
(VI)

in which $R^1$, $Z^1$, $Z^2$ and $Z^3$ are as hereinbefore defined, and M is an alkali metal, preferably lithium with a compound of the formula (VII):

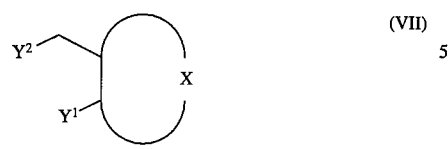
(VII)

in which X and $Y^1$ are as hereinbefore and $Y^2$ which may be the same as or different to $Y^1$, is bromine or iodine, optionally in the presence of metal halide $MY^2$, in a suitable solvent such as THF, at a low temperature which is preferably below –65° C.

The enolate compound of formula (VI) may be conveniently formed in situ, prior to further reaction thereof, by treating a compound of formula (VIII):

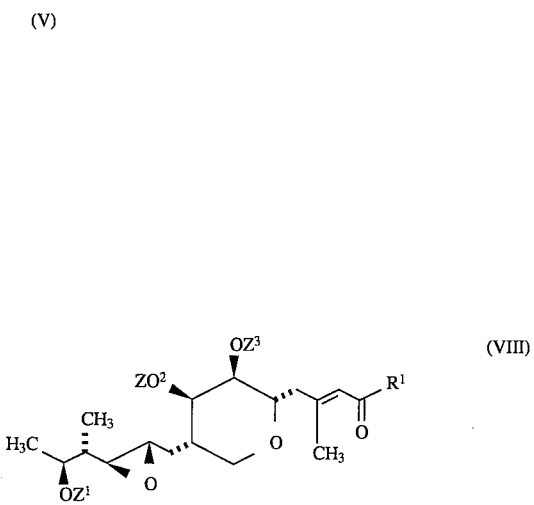
(VIII)

in which $R^1$, $Z^1$, $Z^2$ and $Z^3$ are as hereinbefore defined with an enolising agent such as an non-nucleophilic organic base, for instance lithium diisopropylamide or lithium hexamethyl disilylazide, which may be conveniently formed in situ as a preliminary step.

Compounds of formula (VII) are either commercially available or readily obtainable from commercially available starting materials by conventional synthetic procedures well known to those skilled in the art.

A compound of formula (VIII) in which $R^1$ is $N(OR^2)R^3$ or $NR^4R^5$ may suitably be obtained from monic acid by treatment thereof with iso-butyl chloroformate in tetrahydrofuran, in the presence of triethylamine, at a temperature of from –5° to 20° C. for about 30 min. to form an intermediate mixed anhydride (monic acid isobutyl carbonic anhydride). This intermediate may then be reacted with an amine $HN(OR^2)R^3$ in dichloromethane at about 20° C. for about 2 h or an amine $HNR^4R^5 \cdot HCl$ in the presence of triethylamine and 4-dimethylaminopyridine, in THF, at about 20° C., to form the compound of formula (VIII) in which $Z^1$, $Z^2$ and $Z^3$ is each hydrogen; in which $R^3$, $R^5$ and $R^6$ are as hereinbefore defined. The hydroxyl groups thereof may be protected by treatment with a suitable hydroxyl protecting agent such as chlorotrimethylsilane, in a solvent such as THF in the presence of methylamine and 4-dimethylamino pyridine as a catalyst. A compound of formula (VIII) in which $R^1$ is $OR^6$ may be prepared by analogy with the processes described by Clayton J. P. et al in J. C. S. Perkin Trans. I, 1979, 308.

Further compounds of formula (I) may be obtained from compounds of formula (I) by suitable functional group interconversion, protecting, if necessary and appropriate, the hydroxyl groups of the moiety of formula (II), as hereinbefore defined.

When used herein for the groups $Z^1$, $Z^2$ and $Z^3$, the term 'hydroxyl-protecting group' refers to any such group known in the art which may be removed without disruption of the remainder of the molecule. Suitable hydroxyl protecting groups include those described in "Protective Groups in Organic Chemistry", Greene and Wuts, John Wiley & Sons, Inc., New York, 2nd edn, 1991.

The hydroxyl groups of monic acid and of the compounds of formulae (I), (III) to (VI), and (VIII) may be protected at any stage of the above processes, using conventional methods. The hydroxyl-protecting group may be removed by methods known in the art, including enzymatic methods.

Particularly suitable hydroxyl-protecting groups are silyl groups since these are readily removed under mild conditions. Such groups are introduced using conventional silylating agents, including halosilanes and silazanes, of the formulae below:

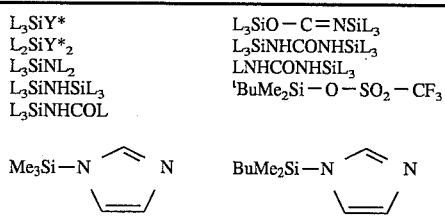

| L₃SiY* | L₃SiO—C=NSiL₃ |
| L₂SiY*₂ | L₃SiNHCONHSiL₃ |
| L₃SiNL₂ | LNHCONHSiL₃ |
| L₃SiNHSiL₃ | ᵗBuMe₂Si—O—SO₂—CF₃ |
| L₃SiNHCOL | | wherein Me denotes methyl and ᵗBu denotes t-butyl, Y* is halogen and each group L is independently selected from hydrogen, $(C_{1-6})$alkyl, $(C_{1-6})$alkoxy, aryl or aryl$(C_{1-4})$alkyl. A preferred silyating agent is trimethylsilyl chloride. Particularly suitable protecting groups are tnmethylsilyl, t-butyldimethylsilyl and t-butyldiphenylsilyl groups. Preferred protecting groups are trimethylsilyl groups because of their ease of removal.

The glycol function of the compounds of formulae (I), (III) to (VI) and (VIII) may be protected by forming a cyclic derivative using a compound of formula (IX):

$$R^7C(OR^8)(OR^9)(OR^{10}) \quad (IX)$$

wherein $R^7$ is hydrogen or $(C_{1-6})$alkyl and each of $R^8$, $R^9$ and $R^{10}$ is $(C_{1-6})$alkyl, such that in the cyclic derivative $Z^1$ and $Z^2$ together are a moiety $R^7C(OR^{10})$. Suitably $R^7$ is hydrogen, methyl, ethyl, n- or iso-propyl; most suitably it is hydrogen. The groups $R^8$, $R^9$ and $R^{10}$ are suitably methyl, ethyl, n- or iso-propyl, or n-, iso-, sec- or t-butyl; most suitably methyl. Similarly the hydroxyl groups of a compound of formula (I) may be protected prior to conversion to a further compound of formula (I) as described above. In each case the hydroxyl protecting groups described above may be removed by mild acid hydrolysis followed by alkaline hydrolysis, for instance, as described by Clayton et al, J. C. S. Perkin Trans I, 1979,308.

The compounds of formula (I) are useful for the treatment of bacterial and mycoplasma-induced infections in non-human and human animals, such as the treatment of respiratory tract infections, otitis, meningitis, skin and soft tissue infections in human animals, mastitis in cattle, and respiratory infections in non-human animals such as pigs and cattle.

Accordingly, in a further aspect, the present invention provides a method for treating the human or non-human animal which method comprises administering a therapeutically effective mount of a compound of formula (I) as hereinbefore defined, to a human or non-human animal in need of such therapy.

In particular aspects of the treatment, there are provided methods for treating bacterial or mycoplasmal infections of human or non-human animals, especially respiratory infections in human or non-human animals.

In an alternative aspect, the present invention provides a compound of formula (I), as hereinbefore defined for use in therapy.

The compounds of this invention are active against both Gram negative and Gram positive organisms, including Haemophilus, for instance *H.infiuenzae* Q1; Moraxella, for instance *M. catarrhalis* 1502; Streptococci, for instance *S.pyogenes* CN10 and *S.pneumonia* PU7. Staphylococci, for instance *S.aureus* Oxford; Legionella, for instance *L.pneumophila*; and against mycoplasma. In addition, compounds of this invention are active against Staphylococci organisms such as *S.aureus* and *S.epidermidis* which are resistant (including multiply-resistant) to other anti-bacterial agents, for instance, β-lactam antibiotics such as, for example, methicillin; macrolides; aminoglycosides and lincosamides.

The compounds of this invention are also active against mycoplasma-induced infections, in particular infections caused by *Mycoplasma fermentans*, which has been implicated as a co-factor in the pathogenesis of AIDS.

Accordingly in a further aspect, the present invention provides a method of treating humans infected with *M. fermentans*, in particular humans also infected with HIV, which method comprises treating humans in need of such therapy with an anti-mycoplasmal effective amount of a compound of formula (I).

This invention also provides a pharmaceutical or veterinary composition which comprises a compound of formula (I) (hereinafter referred to as the 'drug') together with a pharmaceutically or veterinarily acceptable career or excipient.

The compositions may be formulated for administration by any route, and would depend on the disease being treated. The compositions may be in the form of tablets, capsules, powders, granules, lozenges, liquid or gel preparations, such as oral, topical or sterile parenteral suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch, or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl 4-hydroxybenzoate or sorbic acid, and if desired conventional flavouring or colouring agents.

For topical application to the skin the drug may be made up into a cream, lotion or ointment. Cream or ointment formulations that may be used for the drug are conventional formulations well known in the art, for example, as described in standard text books of pharmaceutics and cosmetics, such as 'Harry's Cosmeticology' published by Longman, and the British Pharmacopoeia.

Suppositories will contain conventional suppository bases, e.g. cocoa-butters or other glyceride.

For parenteral administration, fluid unit dosage forms are prepared utilizing the drug and a sterile vehicle. The drug, depending on the vehicle and concentration used, can be suspended in the vehicle. Advantageously, adjuvants such as a local anaesthetic, preservative and buffering agents can be dissolved in the vehicle. To enhance the stability the composition can be frozen after filling into the vial and water removed under vacuum. The dry lypophilized powder is then sealed in the vial. The drug can be sterilised by exposure to ethylene oxide before suspending in the sterile vehicle. Advantageously, a surfactant or wetting agent is included in the composition to facilitate uniform distribution of the drug.

For topical application to the ear, the drug may be made up into a suspension in a suitable liquid carrier, such as water, glycerol, diluted ethanol, propylene glycol, polyethylene glycol or fixed oils. For topical application to the eye, the drug is formulated as a suspension in a suitable, sterile aqueous or non-aqueous vehicle. Additives, for instance buffers such as sodium metabisulphite or disodium edetate; preservatives including bactericidal and fungicidal agents, such as phenylmercuric acetate or nitrate, benzalkonium chloride or chlorhexidine, and thickening agents such as hypromellose may also be included.

The dosage employed for compositions administered topically will, of course, depend on the size of the area being treated. For the ears and eyes each dose will typically be in the range from 10 to 100 mg of the drug.

Veterinary compositions for intramammary treatment of mammary disorders in animals, especially bovine mastitis, will generally contain a suspension of the drug in an oily vehicle.

The compositions may contain from 0.1% to 99% by weight, preferably from 10–60% by weight, of the drug, depending on the method of administration. Where the compositions are in unit dose form, each dosage unit will preferably contain from 50–500 mg, of the drug. The dosage as employed for adult human treatment will preferably range from 100 mg to 3 g, per day, for instance 250 mg to 2 g of the drug per day, depending on the route and frequency of administration.

Alternatively, the drug may be administered to non-human animals as part of the total dietary intake. In this case the amount of drug employed may be less than 1% by weight of the diet and in preferably no more than 0.5% by weight. The diet for animals may consist of normal foodstuffs to which the drug may be added or the drug may be included in a premix for admixture with the foodstuff. A suitable method of administration of the drug to a non-human animal is to add it to the non-human animal's drinking water. In this case a concentration of the drug in the drinking water of about 5–500 µg/ml, for example 5–200 µg/ml, is suitable.

Pharmaceutical or veterinary compositions may also be used in a method of treatment according to the present invention. The present invention further provides for the use of a compound of formula (I) in the manufacture of a medicament for anti-bacterial and/or anti-mycloplasmal therapy of human and non-human animals.

No adverse toxicological effects are effects are expected from the administration of compounds of formula (I).

The following Examples illustrate the invention, but are not intended to limit the scope in any way.

Preparation 1

N-Methoxy-N-methyl-6,7,13-O-tris(trimethylsilyl) monamide-N,O-Dimethyl hydroxylamine hydrochloride (1.95 g, 20 mmol) was dissolved in dichloromethane and aqueous sodium hydroxide (20 ml:10 ml, 2.5M). The aqueous layer was re-extracted with dichloromethane (10 ml) and the combined organic layers washed with saturated brine (5 ml). The organic layer was dried (MgSO$_4$) and added to monic acid isobutyl carbonic anhydride (10 mmol). After stirring at 20° C. for 1 h the reaction mixture was diluted with dichloromethane and washed with saturated aqueous sodium hydrogen carbonate and brine. The combined aqueous solutions were extracted with ethyl acetate, and the combined organic solutions dried (MgSO$_4$) and concentrated to give the amide, (3.0 g). This was taken up in tetrahydrofuran (50 ml) and treated with triethylamine (8.4 ml, 60 mmol) and chlorotrimethylsilane (6.3 ml, 50 mmol). After 10 minutes a catalytic amount of 4-N,N-dimethylaminopyridine was added. After 2 h at room temperature the reaction was diluted with diethyl ether, filtered, and the filtrate evaporated. The residue was taken up in hexane, refiltered, and washed with water and brine. After drying and evaporation the residue was taken up in hexane (20 ml) and allowed to crystallise at 0°–20° C., to give the required product as a colourless crystalline solid (3.0 g, 50%) mp 78°–79° C.

EXAMPLE 1

E-2-(2-[3R,4R-Dihydroxy-5S-(2S,3S-epoxy-5S-hydroxy-4S-methylhexyl)tetrahydropyran-2S-yl)]-(1-methylethyl-idene))indan-1-one.

a) 3-([3R,4R-Bistrimethyisilyloxy-5S-(2S,3S-epoxy-5S-trimethylsilyloxy-4S-methylhexyl)tetrahydropyran-2S-yl]methyl)-[1-R,S-(2-bromobenzyl)]-N-methoxy-N-methyl-but-3-enamide.

Di-iso-propylamine (0.22 ml, 1.6 mmol) and t-butyl lithium (1.7M in hexane) (5.16 ml, 8.8 mmol) were added dropwise sequentially to N-methoxy-N-methyl-6,7,13-O-tris-(trimethylsilyl)monamide (preparation 1,4.80 g, 8.0 mmol) in THF (80 ml) maintaining the temperature at −70° to −65° C. After 45 minutes at −70° C., 2-bromobenzyl bromide (12.00 g, 48.00 mmol) in THF (10 ml) was added, the solution warmed to room temperature then heated to reflux for 48 h. The products were poured into water (100 ml) and extracted with ethyl acetate. Drying (Na$_2$SO$_4$), evaporation to dryness under reduced pressure and flash chromatography using hexane/ethyl acetate (4:1) as eluent gave the title compounds (2.80 g, 45%) as a colourless oil; δH (CDCl$_3$) (one diastereomer) 0.10–0.16 (27H, m, 8×SiCH$_3$), 0.90 (3H, d, J 7.0 Hz, 17-H$_3$), 1.20 (3H, d, J 6.3 Hz, 14-H$_3$), 1.31–1.41 (1H, m, 12-H), 1.54–1.68 ( 2H, m, 9-H$_2$), 1.75–183 (1H, m, 8-H), 2.02 (1H, dd, J 10.8 and 15.4 Hz, 4-H), 2.60 (1H, d, J 15.4 Hz, 4-H),2.63 (2H, m, 10 and 11-H),3.06 (3H, s, N-CH$_3$), 3.06 (1H, dd, J 17.9 and 4.5 Hz, CH$_A$H$_B$Ph), 3.19 (1H, dd, J 17.9 and 10.1 Hz, CH$_A$H$_B$Ph), 3.38 (1H, dd, J 2.3 and 8.9 Hz, 6-H), 3.42 (3H, s, OCH$_3$), 3.52 (1H, d, J 1.3 Hz, 16-H), 3.78–4.03 (5H, m, 5, 7, 13, 16 and 2-H), 5.05 (1H, s, 15-H), 5.09 (1H, s, 15H), 7.04 (1H, dt, J 7.6 and 1.8 Hz, 4' or 5'-H), 7.18 (1H, dt, J 7.6 and 1.8 Hz, 4' or 5'-H), 7.32 (1H, dd, J 7.6 and 1.8 Hz, 6'-H), 7.49 (1H, dd, J 7.6 and 1.8 Hz, 3'-H); (2nd diastereomer) inter alia 2.04 (1H, dd, J 15.2 and 10.6 Hz, 4-H), 2.54 (1H, d, J 15.2 Hz, 4-H), 3.05 (1H, dd, J 4.6 and 13.2 Hz, CH$_A$H$_B$Ph), 3.24 (1H, dd, J 13.2 and 10.3 Hz, (H$_A$H$_B$Ph), 5.11 (1H, s, 15-H), 5.20 ( 1H, s, 15-H), 7.03 (1H, dt, J 7.7 and 1.7 Hz, 4' or 5'-H), 7.18 (1H, dt, J 7.7 and 1.7 Hz, 4' or 5'-H), 7.31 (1H, dd, J 7.7 and 1.7 Hz, 6'-H), 7.50 (1H, dd, J 7.5 and 1.7 Hz, 3'-H), m/z (FAB 3-NOBA/Na) 796 (MNa$^+$, 27%); (Found: (M-CH$_3$)$^+$, 756.2793. C$_{26}$H$_{35}$NO$_7$Br requires M-CH$_3$, 756.2783).

b) 2-R,S-(1-([3R,4R-Bistrimethyisilyloxy-5S-(2S,3S-epoxy-5S-trimethylsilyloxy-4S-methylhexyl)tetrahydropyran-2S-yl]-methyl)ethyl)indan-1-one t-Butyl lithium (1.7M in hexane) (6.40 ml, 10.88 mmol) was added dropwise to the above amide (2.80 g, 3.63 mmol) in THF (30 ml) maintaining the temperature below −65° C. After 1 h at −70° C. acetic acid (0.72 ml. 12.6 mmol) was added dropwise, water then added and the solution extracted with ethyl acetate. Drying (MgSO$_4$), evaporation to dryness under reduced pressure and purification by flash chromatography using hexane/ethyl acetate (6:1) as eluent gave the title compounds (1.97 g, 86%) as a colourless oil; $\delta_H$ (CDCl$_3$) inter alia 0.87 (3H, d, J 7.1 Hz, 17-H$_3$ of one diastereomer), 0.89 (3H, d, J 7.1 Hz, 17-H$_3$ of other diastereomer), 1.19 (3H, d, J 6.3 Hz, 14-H$_3$ of one diastereomer), 1.20 (3H, d, J 6.3 Hz, 14-H$_3$ of other diastereomer), 1.95 (1H, dd, J 10.6 and 15.4 Hz, 4-H of one diastereomer), 2.06 (1H, dd, J 10.6 and 15.3 Hz, 4-H of other diastereomer), 2.45–2.72 (3H, m, 4, 10 and 11-H), 3.10–3.20 (1H, m, 2-H), 3.24–3.45 (4H, m, CH$_2$Ph, 6 and 16-H), 4.96 (1H, s, 15-H), 5.10(s) and 5.15 (s) (1H, 15-H), 7.30–7.79 (4H, m, aromatic); m/z 632 (M$^+$, 2%), 73 (100%); (Found: M$^+$, 532.3375. C$_{33}$H$_{56}$O$_6$Si$_3$ requires M, 532.3385).

c) E-2-(2-[3R,4R-Bistrimethyisilyloxy-5S-(2S,3S-epoxy-5S-trimethylsilyloxy-4S-methylhexyl)tetrahydropyran-2S-yl](1-methylethylidene))indan-1-one Potassium t-butoxide (0.44 g, 3.6 mmol) was added to the above ketone (1.97 g, 2.98 mmol) in THF (40 ml) cooled to −70° C. After 1.5 h at −70° C. acetic acid (0.24 ml, 4.2 mmol) was added dropwise followed by water. Extraction with ethyl acetate, drying (Na$_2$SO$_4$), evaporation to dryness under reduced pressure and purification by flash chromatography using hexane/ethyl acetate (6:1) as eluent gave the title compound (1.65 g, 84%) as a colourless oil; $\delta_H$ (CDCl$_3$), 0.10–0.16 (27H, m, 9×SiCH$_3$), 0.90 (3H, d, J 7.0 Hz, 17-H$_3$), 1.20 (3H, d, J 6.3 Hz, 14-H$_3$), 1.33–1.45 (1H, m, 12-H), 1.48–1.59 (2H, m, 9-H$_2$), 1.78–1.95 (1H, m, 8-H), 2.26 (1H, dd, J 10.6 and 13.5 Hz, 4-H), 2.48 (3H, s, 15-H$_3$), 2.59 (1H, d, J 13.4 Hz, 4-H), 2.67–2.73 (2H, m, 10 and 11-H), 3.40–3.45 (1H, m, 6-H), 3.47 (1H, d, J 11.5 Hz. 16-H), 3.62 (1H, d, J 20.1 Hz. CH$_A$H$_B$Ph), 3.76 (1H, d, J 20.1 Hz, CH$_A$H$_B$Ph), 3.82–3.93 (4H, m, 5, 7, 13, 16-H), 7.35 (1H, t, J 7.3 Hz, phenyl), 7.45 (1H, d, J 7.3 Hz, phenyl), 7.54 (1H, t, J 7.3 Hz, phenyl), 7.80 (1H, d, J 7.3 Hz, phenyl); m/z 632 (M$^+$, 3%), 117 (100%); (Found: M$^+$, 632.3394. C$_{33}$H$_{56}$O$_6$Si$_3$ requires M, 632.3385).

d) E-2-(2-[3R,4R-Dihydroxy-5S-(2S,3S-epoxy-5S-hydroxy- 4S-methyl-hexyl)tetrahydropyran-2S-yl)]-(1-methylethylidene))indan-1-one The above ketone (1.37 g, 2.17 mmol) and 4-dimethylaminopyridine dihydrochloride (11.5 mg, 0.06 mmol) in methanol (25 ml) were stirred at room temperature for 1 h. Saturated sodium hydrogen carbonate solution was added and the solution extracted with ethyl acetic. Drying (Na$_2$SO$_4$), evaporation to dryness under reduced pressure and purification by flash chromatography using 7% methanol in dichloromethane as eluent and recrystallisation from ethyl acetate gave the title compound (0.72 g, 80%) as white micro-needles (mp. 146°–7° C.); $\lambda_{max}$ (EtOH) 280.5 nm ($\epsilon_m$ 19.644); $\delta_H$(CD$_3$OD) 0.94 (3H, d, J 7.1 Hz. 17-H$_3$), 1.20 (3H, d, J 6.3 Hz. 14-H$_3$), 1.34–1.47 (1H, m, 12-H), 1.63–1.82 (2H, m, 9-H$_2$), 1.91–2.01 (1H, m, 8-H), 2.45 (3H, s, 15-H$_3$), 2.47 (1H, dd, J 13.8 and 9.8 Hz, 4-H), 2.70–2.84 (3H, m, 4, 10 and 11-H). 3.42 (1H, dd, J 9.2 and 3.0 Hz, 16-H), 3.54 (1H, d, J 11.6 Hz. 16-H), 3.68–3.93 (6H, m, 5, 7, 13, 16-H and CH$_2$Ph), 7.39 (1H, t, J 7.3 Hz, phenyl), 7.51–7.63 (2H,m, phenyl), 7.71 (1H, d, J 7.3 Hz, phenyl); $\delta_C$ (CD$_3$OD) 12.3 (C-17), 19.2 (C-15), 20.4 (C-14), 33.1 (C-9), 33.1 (CH$_2$Ph), 40.7 (C-4), 40.7 (C-8), 43.7 (C-12), 56.7 (C-10), 61.3 (C-11), 66.5 (C-16), 70.4(C-6), 70.7 (C-7), 71.7 (C-13), 77.0 (C-5), 124.5, 127.3, 128.3, 133.4 (C-2), 135.3, 141.1 (quat.), 150.2 (quat.), 153.6 (C-3), 196.2 (C-1); m/z 416 (M$^+$, 3%), 172 (100%); (Found: C, 68.98; H 7.58. C$_{24}$H$_{32}$O$_6$ requires C, 69.21; H 7.75%).

EXAMPLE 2

E-2-(2-[3R,4R-Dihydroxy-5S-(2S,3S-epoxy-5S-hydroxy-4S-methylhexyl)-tetrahydropyran-2S-yl)]-(1-methylethyl-idene))-5-methoxyindan-1-one a) 2-R,S-(1-([3R,4R-Bistrimethyisilyloxy-5S-(2S,3S-epoxy- 5S-trimethylsilyloxy-4S-methylhexyl)tetrahydropyran-2S-yl]methyl)-ethenyl)- 5-methoxyindan-1-one Diisopropylamine (0.16 ml, 1.7 mmol) and t-butyl lithium (1.7M in hexane) (3.88 ml, 6.6 mmol) were added dropwise sequentially to N-methoxy-N-methyl-6, 7, 13-O-tris(trimethylsilyl)monamide (3.61 g, 6.0 mmol) in THF (30 ml) maintaining the temperature at −70° to −65° C. After 1 h at −70° C. 2-bromo-5-methoxybenzyl bromide (6.72 g, 24.0 mmol) in THF (10ml) and lithium iodide (0.40 g, 2.99 mmol) were added and the solution heated to reflux for 48 h. Water was added and the products extracted with ethyl acetate. Drying (Na$_2$SO$_4$), evaporation to dryness and purification by flash chromatography gave the impure required alkylated products (2.78 g). t-Butyl lithium (1.7M in hexane) (5.10 ml, 8.66 mmol) was added dropwise to this product in THF (30 ml) maintaining the temperature below −70° C. After 2 h at −70° C. acetic acid (0.56 ml, 9.80 mmol) was added followed by water. Extraction with ethyl acetate, drying (Na$_2$SO$_4$), evaporation to dryness under reduced pressure and purification by flash chromatography using hexane/ethyl acetate (4:1) as eluent gave the title compounds (1.51 g, 38%) as a colourless oil; $\delta$H (CDCl$_3$) (one diastereomer) 0.10–0.16 (27H, m, 9×SiCH$_3$), 0.88 (3H, d, 17-H$_3$), 1.19 (3H, d, J 6.3 Hz, 14-H$_3$), 1.34–1.39 (1H, m, 12-H), 1.47–1.56 (2H, m, 9-H$_2$), 1.71–1.85 (1H, m, 8-H), 2.06 (1H, dd, J 15.0 and 10.5 Hz, 4-H), 2.50 (1H, d, J 15.0 Hz, 4-H), 2.62–2.66 (2H, m, 10 and 11-H), 3.09 (1H, dd, J 17.2 and 3.9 Hz, 2-H), 3.28–3.45 (4H, m, 6.16-H and CH$_2$Ph) 3.68–3.89 (4H, m, 5, 7, 13 and 16-H), 3.87 (3H, s, OCH$_3$), 4.94 (1H, s, 15-H), 5.08 (1H, s, 15-H), 6.85–689 (2H, m, aromatic), 7.69 (1H, d, J 9.0 Hz, aromatic); (other diastereomer) inter alia 1.91 (1H, dd, J 15.4 and 10.5 Hz. 4-H), 2.51 (1H, d, J 15.4 Hz, 4-H), 3.07 (1H, dd, J 17.3 and 3.6 Hz, 2-H), 3.29–3.43 (3H, m, 6-H and CH$_2$Ph), 3.46 (1H, d, J 11.3 Hz, 16-H), 4.95 (1H, s, 15-H), 5.07 (1H, s, 15-H); m/z 662 (M$^+$, 17%), 117 (100%); (Found: M$^+$, 662.3487. C$_{34}$H$_{58}$O$_7$Si$_3$ requires M, 662.3490).

b) E-2-(2-[3R,4R-Bistrimethyisilyloxy-5S(2S,3S-epoxy-5S-trimethylsilyloxy- 4S-methylhexyl)tetrahydropyran-2S-yl]-(1-methylethylidene))-5-methoxyindan1-one Potassium t-butoxide (0.24 g, 1.93 mmol) was added to the above ketone (1.16 g, 1.75 mmol) in THF (25 ml) cooled to −70° C. After 2 h at −70° C. acetic acid (0.12 ml, 1.90 mmol) was added followed by water. Extraction with ethyl acetate drying (Na$_2$SO$_4$), evaporation to dryness under reduced pressure and purification by flash chromatography using hexane/ethyl acetate (5:1) as eluent gave the title compound (0.92 g, 80%) as a colourless oil; $\delta$H (CDCl$_3$) 0.10–0.16 (27H, m, 9×SiCH$_3$), 0.90 (3H, d, J 7.0 Hz, 17-H$_3$), 1.20 (3H, d, J 6.3 Hz, 14-H$_3$), 1.35–1.43 (1H, m, 12-H), 1.50–1.62 (2H, m, 9-H$_2$), 1.85–191 (1H, m, 8-H), 2.23 (1H, dd, J 13.5 and 10.5 Hz. 4-H), 2.45 (3H, s, 15-H$_3$), 2.55 (1H, d, J 13.5 Hz, 4-H), 2.67–2.72 (2H, m, 10 and 1 11-H), 3.42 (1H, dd, J 9.0 and 2.4 Hz, 6-H), 3.47 (1H, d, J 11.4 Hz, 16-H), 3.57 (1H, d, J 20.0 Hz, CH$_A$H$_B$Ph), 3.70 (1H, d, J 20.0 Hz, CH$_A$H$_B$Ph), 3.81–3.90 (4H, m, 5, 7, 13 and 16-H), 3.88 (3H, s, OCH$_3$), 6.88–6.90 (2H, m, aromatic), 7.73 (1H, d, J 9.1 Hz, aromatic); m/z 662 (M$^+$, 3%), 73 (100%); (Found: M$^+$, 662.3500. C$_{34}$H$_{58}$O$_7$Si$_3$ requires M, 662.3490).

c) E-2-(2-[3R,4R-Dihydroxy-5S-(2S,3S-epoxy- 5S-hydroxy- 4S-methylhexyl)tetrahydropyran-2S-yl)]-(1-methylethylidene))- 5-methoxyindan-1-one The above ketone (0.91 g, 1.37 mmol) and 4-dimethylamino pyridine dihydrochloride (8.0 mg, 0.04 mmol) in methanol (25 ml) were stirred at room temperature for 1 h. Saturated sodium hydrogen carbonate solution was added and the solution extracted with ethyl acetate. Drying ($Na_2SO_4$), evaporation to dryness under reduced pressure and purification by flash chromatography using 7% methanol in dichloromethane as eluent followed by recrystallisation from hexane/ethyl acetate gave the title compound (0.56 g, 92%) as white micro-needles (m.p. 118°–119° C.); $\nu_{max}$ (KBr) 3425, 2968, 2921, 1675, 1623, 1599, 1302, 1257, 1090 cm$^{-1}$; $\lambda_{max}$ (EtOH) 307.0 nm ($\epsilon_m$ 20,300); $\delta_H$ ($CD_3OD$) 0.94 (3H, d, J 7.0 Hz, 17-$H_3$), 1.20 (3H, d. J 6.5 Hz, 14-$H_3$), 1.33–1.47 (1H, m, 12-H), 1.60–1.82 (2H, m, 9-$H_2$), 1.87–1.98 (1H, m, 8-H), 2.43 (3H, s, 15-$H_3$), 2.46 (1H, dd, J 13.5 and 9.7 Hz, 4-H), 2.67–2.84 (3H, m, 10, 11 and 4-H), 3.42 (1H, dd, J 9.3 and 3.1 Hz, 6-H). 3.54 (1H, d, J 11.5 Hz 16-H), 3.66 (1H, d, J 20.5 Hz, $CH_AH_BPh$), 3.77 (1H, d. J 20.5 Hz, $CH_AH_Bph$), 3.76–3.92 (CH, m, 5, 7, 13, 16-H), 3.88 (3H, s, $OCH_3$), 6.93 (1H, dd, J 8.6 and 2.0 Hz, phenyl), 7.01 (1H, d, J 2.0 Hz, phenyl), 7.64 (1H, d, J 8.6 Hz, phenyl): $\delta_C$ ($CD_3OD$) 12.3 (C-17), 18.9 (C-15), 20.4 (C-14), 33.1 (C-9), 33.2 ($CH_2Ph$), 41.7 (C-4), 41.9 (C-8), 43.7 (C-12), 56.2 ($OCH_3$), 56.7 (C-10), 61.3 (C-11), 66.5 (C-16), 70.4 (C-6), 70.7 (C-7), 71.7 (C-13), 77.0 (C-5), 110.3, 116.3, 126.3, 133.6 (C-2), 134.5 (quat.), 151.8 (quat.), 153.2 (C-3), 166.6 (quat.), 195.1 (C-1); m/z (FAB, thioglycerol) 447 ($MH^+$, 100%); (Found: C, 66.88; H, 7.85. $C_{25}H_{34}O_7$ requires C, 67.2; H, 7.85).

EXAMPLE 3

E-2-(2-[3R,4R-Dihydroxy-5S-(2S,3S-epoxy-5S-hydroxy-4S-methylhexyl)tetrahydropyran-2S-yl)]-(1-methylethyl-idene))-7-methylindan-1-one a) E-2-(2-[3R,4R-Bistrimethylsilyloxy-5S-(2S,3S-epoxy-5S-trimethylsilyloxy-4S-methylhexyl)tetra hydropyran-2S-yl]-( 1-methylethylidene))-7-methylindan-1-one Diisopropylamine (0.16 ml, 1.2 mmol) and t-butyl lithium (1.7M in hexane) (3.88 ml, 6.6 mmol) were added dropwise sequentially to N-methoxy-N-methyl-6,7,13-O-tris-trimethylsilyl)monamide ( 3.61 g, 6.00 mmol) in THF (30 ml) maintaining the temperature below –65° C. After 1 h at –70° C., 2-bromo-3-methylbenzyl bromide (6.33 g, 24.0 mmol) and lithium iodide (2.00 g, 14.5 mmol) were added and the solution heated to reflux for 60 h. The products were poured into water and extracted with ethyl acetate, dried ($Na_2SO_4$) and evaporated to dryness under reduced pressure. Purification by flash chromatography using hexane/ethyl acetate (3:1) as eluent gave impure product (2.13 g) of the same $R_f$ as the starting amide. t-Butyl lithium (1.7M in hexane) (3.97 ml, 6.75 mmol) was added to the impure products (2.13 g) in THF (20 ml) maintaining the temperature below –65° C. After 2 h at –70° C. acetic acid (0.39 ml, 6.75 mmol) then water were added. Extraction with ethyl acetate, drying ($Na_2SO_4$), evaporation to dryness under reduced pressure and purification by flash chromatography using hexane/ethyl acetate (6:1) as eluent gave a mixture of the deconjugated ketones and the required ketone (0.68 g, 18%). This mixture was treated with potassium t-butoxide (0.14 g, 1.14 mmol) in THF (20 ml) at –70° C. for 2 h. Acetic acid (0.08 ml, 1.40 mmol) then water were added. Extraction with ethyl acetate, drying ($Na_2SO_4$), evaporation to dryness under reduced pressure and purification by flash chromatography using hexane/ethyl acetate (9:1) as eluent gave the title compound (0.41 g, 62%) as a colourless oil; $\delta_H$ ($CD_3OD$) 0.11–0.17 (27H, m, 9×$SiCH_3$), 0.93 (3H, d, J 7.0 Hz, 17-$H_3$), 1.19 (3H, d, J 6.3 Hz, 14-$H_3$), 1.33–1.43 (1H, m, 12-H), 1.58–1.87 (3H, m, 9-$H_2$ and 8-H), 2.35 (1H, dd, J 13.6 and 10.5 Hz, 4-H), 2.40 (3H, s, 15-$H_3$), 2.59 (1H, d, J 13.0 Hz, 4-H), 2.63 (3H, s, $PhCH_3$), 2.72–2.79 (2H, m, 10 and 11-H), 3.51 (1H, d, J 11.5 Hz, 16-H), 3.57 (1H, dd, J 8.9 and 2.6 Hz, 6-H), 3.61 (1H, d, J 20.1 Hz. $CH_AH_BPh$), 3.73 (1H, d, J 20.1 Hz, $CH_AH_BPh$), 7.11 (1H, d, J 7.5 Hz, phenyl), 7.30 (1H, d, J 7.5 Hz. phenyl), 7.44 (1H, t, J 7.5 Hz, phenyl): m/z 646 ($M^+$, 12%), 73 (100%); (Found: $M^+$, 646.3536. $C_{34}H_{58}O_6Si_3$ requires M, 646.3541).

b) E-2-(2-[3R,4R-Dihydroxy-5S-(2S,3S-epoxy-5S-hydroxy- 4S-methylhexyl)tetrahydropyran-2S-yl)]-(1-methylethylidene))- 7-methylindan-1-one The above ketone (0.40 g, 0.62 mmol) and 4-dimethylaminopyridine dihydrochloride (4.0 mg, 0.02 mmol) in methanol (20 ml) were stirred at room temperature for 1 h. Addition of saturated sodium hydrogen carbonate solution, extraction with ethyl acetate, drying ($Na_2SO_4$), evaporation to dryness under reduced pressure and purification by flash chromatography using 7% methanol in dichloromethane as eluent gave the title compound (0.20 g, 74%) as a white foam; $\nu_{max}$ (KBr) 3437, 2972, 2878, 1680, 1674, 1595 cm$^{-1}$; $\lambda_{max}$ (EtOH) 279.5 nm ($\epsilon_m$ 19,570); $\delta_H$ ($CD_3OD$) 0.94 (3H, d, J 7.1 Hz. 17-$H_3$), 1.20 (3H, d, J 6.3 Hz, 14-$H_3$), 1.35–1.45 (1H, m, 12H), 1.65–1.79 (2H, m, 9-$H_2$), 1.92–1.97 (1H, m, 8-H), 2.41 (3H, s, 15-$H_3$), 2.43 (1H, dd, J 13.7 and 9.4 Hz, 4-H), 2.60 (3H, s, $PhCH_3$), 2.70–2.74 (2H, m, 4 and 11-H), 2.81 (1H, dt, J 6.0 and 2.1 Hz, 10-H), 3.43 (1H, dd, J 9.1 and 3.0 Hz, 6-H), 3.55 (1H, d, J 11.5 Hz, 16-H), 3.60 (1H, d, J 20.6 Hz, $CH_AH_BPh$), 3.70 (1H, d, J 20.6 Hz, $CH_AH_BPh$), 3.75–3.92 (4H, m, 5, 7, 13, 16-H), 7.06 (1H, d, J 7.4 Hz, phenyl), 7.25 (1H, d, J 7.4 Hz, phenyl), 7.38 (1H, t, J 7.4 Hz, phenyl); $\delta_C$ ($CD_3OD$) 12.3 (C-17), 18.6 ($PhCH_3$), 18.9 (C-15), 20.4 (C-14), 32.7 ($CH_2Ph$), 33.1 (C-9), 41.7 (C-4), 41.8 (C-8), 43.7 (C-12), 56,7 (C-10), 61.3 (C-11, 66.5 (C-16), 70.4 (C-6), 70.7 (C-7), 71.7 (C-13), 77.0 (C-5), 124.5, 130.1, 133.7 (C-2), 134.6, 138.4 (quat.), 139.6 (quat.), 150.8 (quat.), 151.5 (C-3), 197.3 (C-1); m/z 430 ($M^+$, 5%), 197 (100%); (Found: $M^+$, 430.2368. $C_{25}H_{34}O_6$ requires M, 430.2355),

EXAMPLE 4

E-2-(2-[3R,4R-Dihydroxy-5S-(2S,3S-epoxy-5S-hydroxy-4S-methylhexyl)tetra hydropyran-2S-yl)]-(1-methylethyl-idene))- 7-methoxyindan-1-one a)2-Bromo-3-methoxybenzyl bromide 2-Bromo-3-methylanisole (2.02 g, 1.00 mmol) and N-bromosuccinimide in carbon tetrachloride (25 ml) were heated to reflux over a 150 W light bulb for 2 h. The solution was cooled to 5° C., filtered and evaporated to drynes under reduced pressure. Purification by flash chromatography using hexane/dichloromethane (8:1) as eluent gave the title compound (162 g, 58%) as a white low melting point solid; $\delta_H$ ($CDCl_3$) 3.90 (3H, s, $OCH_3$), 4.64 (2H, s, $CH_2Br$), 6.85 (1H, dd, J 8.2 and 1.3 Hz, 6-H), 7.08 (1H, dd, J 7.5 and 1.3 Hz, 4-H9, 7.23–7.30 (1H, m, 5-H): $\delta_C$ ($CDCl_3$) 33.7 ($CH_2Br$), 56.4 ($OCH_3$), 111.8, 114.1 (C-2), 123.1, 128.3, 138.6 (C-1), 156.4 (C-3): m/z 282 ($M^+$, 12%), 280 ($M^+$, 13%). 199 (100%): (Found: $M^+$, 277.8947. $C_8H_8OBr_2$ requires M, 277.8942).

b) E-2-(2-[3R,4R-Bistrimethylsilyloxy-5S-(2S,3S-epoxy-5S-trimethylsilyloxy-4S-methylhexyl)tetrahydropyran-2S-yl]-(1-methylethylidene))-7-methoxyindan-1-one Diisopropylamine (0.08 ml, 0.58 mmol) and t-butyl lithium (1.7M in hexane (3.53 ml, 6.00 mmol) were added dropwise sequentially to N-methoxy-N-methyl-6, 7, 13-O-tristrimethylsilyl)monamide (3.29 g, 5.46 mmol) in THF (30 ml) maintaining the temperature below −65° C. After 1 h at −70° C. 2-bromo-3-methoxybenzyl bromide (1.53 g, 5.46 mmol) and lithium iodide (0.40 g, 3.63 mmol) were added and the mixture heated to reflux for 60 h. The products were poured into water and extracted with ethyl acetate, dried (Na$_2$SO$_4$) and evaporated to dryness under reduced pressure. Removal of the excess benzyl bromide present by flash chromatography using hexane/ethyl acetate (3:1) as eluent gave a complex mixture (1.30 g). This mixture was treated with t-butyl lithium (1.7M in hexane) (2.10 ml, 3.56 mmol) in THF (20 ml) at −70° C. for 2 h. Addition of water, extraction with ethyl acetate, drying (Na$_2$SO$_4$), evaporation to dryness under reduced pressure and purification by flash chromatography using hexane/ethyl acetate (4:1) as eluent gave a complex mixture containing the required deconjugated ketones (0.15 g). This mixture was treated with potassium t-butoxide (0.24 g, 0.36 mmol) in THF (10 ml) at −70° C. for 2 h. Acetic acid (0.020 ml, 0.36 mmol) then water were added. Extraction with ethyl acetate, drying (Na$_2$SO$_4$), evaporation to dryness under reduced pressure and purification by flash chromatography using hexane/ethyl acetate (4:1) as eluent gave the title compound (0.050 g, 1.4%) as a white foam: δ$_H$ (CD$_3$OD) 0.10–0.17 (27H, m, 9×SiCH$_3$), 0.92 (3H, d, J 7.0 Hz, 17-H$_3$), 1.19 ( 3H, d, J 7.0 Hz, 17-H$_3$), 1.19 (3H, d, J 6.3 Hz, 14-H$_3$), 1.33–1.41 (1H, m, 12-H), 1.69–1.88 (3H, m, 9-H$_2$ and 8-H), 2.34 (1H, dd, J 13.4 and 10.5 Hz, 4-H), 2.39 (3H, s, 15-H$_3$), 2.58 (1H, d 13.4 Hz, 4-H), 2.72–2.80 (2H, m, 10 and 11-H), 3.40–3.94 (8H, m, 5, 7, 13, 16-H, 16-H$_2$ and CH$_2$Ph), 3.90 (3H, s, OCH$_3$), 6.91 (1H, d, J 7.9 Hz, phenyl), 7.04 (1H, d, J 7.9 Hz, phenyl), 7.55 (1H, t, J 7.9 Hz, phenyl); m/z 662 (M$^+$, 35%), 73 (100%); (Found: M$^+$, 662.3501. C$_{34}$H$_{58}$O$_7$Si$_3$ requires M, 662.3490).

c) E-2-(2-[3R,4R-Dihydroxy-5S-(2S,3S-epoxy-5S-hydroxy-4S-methylhexyl)tetrahydropyran-2S-yl)]-(1-methylethylidene))-7-methoxyindan-1-one The above ketone (0.050 g, 0.075 mmol) and a catalytic amount of 4-dimethylaminopyridine dihydrochloride were stirred at room temperature for 30 min. Addition of saturated sodium hydrogen carbonate solution, extraction with ethyl acetate, drying (Na$_2$SO$_4$) evaporation to dryness under reduced pressure, and purification by flash chromatography using ethyl acetate/hexane (3:1) as eluent gave the title compound (0.026 g, 77%) as a white foam: ν$_{max}$ (KBr) 3431, 2967, 2929, 1676, 1625, 1597, 1480, 1272, 1066 cm$^{-1}$; λ$_{max}$ (EtOH) 324.5 nm (ε$_m$ 5,567) and 275 nm (ε$_m$ 13,063); λ$_H$ (CD$_3$OD) 0.94 (3H, d, J 7.1 Hz, 17-H$_3$), 1.19 (3H, d, J 6.4 Hz, 14-H$_3$), 1.33–1.44 (1H, m, 12-H), 1.65–1.82 (2H, m, 9-H$_2$), 1.87–1.97 (1H, m, 8-H), 2.41 (3H, s, 15-H$_3$), 2.42 (1H, dd, J 13.6 and 9.6 Hz, 4-H), 2.70–2.84 (3H, m, 4, 10 and 11-H), 3.41 (1H, dd, J 9.3 and 3.0 Hz, 6-H), 3.54 (1H, d, J 11.6 Hz, 16-H), 3.69–3.92 (6H, m, 5, 7, 13, 16-H and CH$_2$Ph), 3.89 (3H, s, OCH$_3$), 6.90 (1H, d, J 8.0 Hz, phenyl), 7.04 (1H, d, J 8.0 Hz, phenyl), 7.54 (1H, t, J 8.0 Hz, phenyl); m/z 446 (M$^+$, 8%); (Found: M$^+$, 446.2305. C$_{25}$H$_{34}$O$_7$ requires M, 446.2305).

EXAMPLE 5

E-5-(2-[3R,4R-Dihydroxy-5S-(2S,3S-epoxy-5S-hydroxy-4S-methylhexyl)tetrahydropyran-2S-yl]-(1-methylethylidene))-5,6-dihydro-4H-cyciopenta[c]furan-4-one a) 3-Bromo-4-hydroxymethylfuran t-Butyl lithium (1.7M in hexane) (29.23 ml, 49.7 mmol) was added dropwise to 3,4-dibromofuran (11.23 g, 49.7 mmol) in THF (120 ml) maintaining the temperature below −65° C. After 1 h at −70° C. dimethylaminoformamide (7.70 ml, 99.4 mmol) was added dropwise. After 2 h at −70° C. the solution was warmed to room temperature, acidified with 6N hydrochloric acid and the solution extracted with ethyl acetate. Drying (Na$_2$SO$_4$), evaporation to dryness under reduced pressure and purification by flash chromatography using hexane/dichloromethane (1:1) as eluent gave a mixture (3:1) of 3-bromofuran-4-carboxaldehyde and 3,4-dibromofuran-2-carboxaldehyde (4.36 g). This mixture (4.36 g) was treated with sodium borohydride (0.54 g, 14.25 mmol) in aqueous ethanol (4:1) (50ml) at 5° C. After 2 h at 5° C. the mixture was acidified with 6N hydrochloric acid and the solution extracted with ethyl acetate. Drying (Na$_2$SO$_4$), evaporation to dryness under reduced pressure and purification by flash chromatography using dichloromethane/hexane (4:1) as eluent gave the title compound (1.55 g, 18%) as an amorphous yellow solid; δ$_H$ (CDCl$_3$) 1.74 (1H, br, s, OH), 4.54 (2H, s, CH$_2$), 7.40–7.47 (2H, m, 2 and 5-H); δ$_C$ (CDCl$_3$) 55.4 (CH$_2$), 100.7 (C-3), 125.4 (C-4), 141.1, 141.5; m/z 178 (M$^+$, 97%), 176 (100%); (Found: M$^+$, 175.9476. C$_5$H$_5$O$_2$Br requires M, 175.9473).

b) 5-R,S-(1-([3R,4R-Bis-trimethylsilyloxy-5S(2S,3S-epoxy-5S-trimethylsilyloxy-4S-methylhexyl)tetrahydropyran-2S-yl]methyl)ethenyl)5,6-dihydro-4H-cyclopenta[c]furan-4-one Phosphorus tribromide (0.89 g, 3.27 mmol) in ether (5 ml) was added dropwise to 3-bromo-4-hydroxymethylfuran(1.45 g, 8.19 mmol) in ether (20 ml) at 5° C. After stirring for 1 h at room temperature excess sodium hydroxide solution (40%) was added. Extraction with ether, drying (Na$_2$SO$_4$) and evaporation to dryness under reduced pressure gave the crude bromomethyl furan (1.65 g) as a brown liquid [δ$_H$ (CDCl$_3$) 4.31 (2H, s, CH$_2$), 6.64 (1H, d, J 1.9 Hz, 2 or 5-H), 6.70 (1H, d, J 1.7 Hz, 2 or 5-H)]. Diisopropylamine (0.16 ml, 1.2 mmol and t-butyl lithium (1.7M in hexane) (3.70 ml, 6.30 mmol) were added dropwise sequentially to N-methoxy-N-methyl-6, 7, 13-O-tristrimethylsilyl monamide (3.61 g, 6.00 mmol) in THF (50 ml) maintaining the temperature below −65° C. After 1 h at −70° C. the crude 3-bromo-4-bromomethylfuran (1.65 g, 6.88 mmol) in THF (5ml) was added dropwise. After stirring at room temperature for 48 h. water was added and the solution extracted with ethyl acetate. Drying (Na$_2$SO$_4$), evaporation to dryness under reduced pressure and purification by flash chromatography using hexane/ethyl acetate as eluent gave the alkylated amide required (2.00 g) still containing some of the starting monamide. t-Butyl lithium (1.7M in hexane) (4.51 ml, 7.68 mmol) was added dropwise to this mixture maintaining the temperature below −80° C. After 30 min. acetic acid (0.44 ml, 7.59 mmol) then water were added. Extraction with ethyl acetate, drying (Na$_2$SO$_4$), evaporation to dryness under reduced pressure and purification by flash chromatography using hexane/ethyl acetate (6:1) as eluent gave the title compounds (0.91 g, 24%) as a colourless oil; δ$_H$ (CD$_3$OD) inter alia 0.10–0.16 (27H, m, 9×SiCH$_3$) 0.89–0.95 (3H, m, 17-H$_3$), 1.17–1.20 (3H, m, 14-H$_3$), 1.28–1.35 (1H, m, 12-H), 1.57–1.86 (3H, m, 8-H and 9-H$_2$), 1.91–2.12 (1H, m, 4-H), 2.48 (1H, d, J 15.0 Hz, 4-H), 2.65–2.74 (2H, m, 10 and 11-H), 4.96 (1H, s, 15-H), 5.03 (s) and 5.07 (s) (1H, 15-H), 7.42 (d, J 1.0 Hz) and 7.45 (d, J 1.0 Hz) (1H, furyl-H), 7.95 (d, J 0.7 Hz) and 7.97 (d, J 0.7 Hz) (1H, furyl-H); m/z 622 (M$^+$, 18%), 73 (100%); (Found: M$^+$, 622.3180. C$_{31}$H$_{54}$O$_7$Si$_3$ requires M, 622.3177).

c) E-5-(2-[3R,4R-Bistrimethyisilyloxy-5S-(2S,3S-epoxy-5S-trimethylsilyloxy-4S-methylhexyl)tetrahydropyran-2S- yl]-(1-methylethylidene))-5,6-dihydro-4H-cyclopenta[c]furan-4-one

Potassium t-butoxide (0.175 g, 1.56 mmol) was added to the above ketone (0.90 g, 1.47 mmol) in THF (20 ml) at −70° C. After 2 h at −70° C. acetic acid (0.09 ml, 1.57 mmol) then water were added and the products extracted with ethyl acetate. Drying ($Na_2SO_4$), evaporation to dryness under reduced pressure and purification by flash chromatography using hexane/ethyl acetate (8:1) as eluent gave the title compound (0.72 g, 80%) as a colourless oil; $\delta_H$ ($CD_3OD$) 0.11–0.17 (27H, m. 9×$SiCH_3$), 0.93 (3H, d, J 7.1 Hz, 17-$H_3$), 1.19 (3H, d, J 6.3 Hz, 14-$H_3$), 1.33–1.41 (1H, m, 12-H), 1.66–1.81 (3H, m, 8-H and 9-$H_2$), 2.29 (1H, dd, J 13.5 and 10.5 Hz, 4-H), 2.36 (3H, s, 15$H_3$), 2.54 (1H, d, J 13.5 Hz, 4-H), 2.72–2.79 (2H, m, 10 and 11-H), 3.47–3.68 (4H, m, 6.16-H and $CH_AH_B$ furyl), 3.84–3.93 (4H, m, 5,7,13 and 16-H), 7.43 (1H, d, J 0.9 Hz, furyl), 7.95 (1H, s, furyl); m/z 622 ($M^+$, 8%), 73 (100%); (Found: $M^+$, 622.3177. $C_{37}H_{54}O_7Si_3$ requires M, 622.3179).

d) E-5-(2-[3R,4R-Dihydroxy-5S-(2S,3S-epoxy-5S-hydroxy-4S-methylhexyl)tetrahydropyran-2S-yl]-(1-methylethylidene)-5,6-dihydro-4H-cyclopenta[c]furan-4-one The above ketone (0.72 g, 1.14 mmol) and 4-dimethylaminopyridine dihydrochloride (7.0 mg, 0.036 mmol) in methanol were stirred at room temperature for 30 min. Saturated sodium hydrogen carbonate solution was added. Extraction with ethyl acetate, drying ($Na_2SO_4$), evaporation to dryness under reduced pressure, purification by flash chromatography using 7% methanol in dichloromethane as eluent followed by recrystallisation from ethyl acetate gave the title compound (0.38 g, 81%) as white micro-needles (m.p. $^{163}$−4° C.); $v_{max}$ (KBr) 3499, 2979, 2919, 2813, 2870, 1690, 1624, 1604, 1535, 1111, 908, 822, 706 cm$^{-1}$; $\lambda_{max}$ (EtOH) 296 nm ($\epsilon_m$ 8,728), 280 nm ($\epsilon_m$ 9,534), 271.5 nm ($\epsilon_m$ 9,955) and 246.5 nm ($\epsilon_m$ 10,060); $\delta_H$ ($CD_3OD$) 0.95 (3H, d, J 7.0 Hz, 17-$H_3$), 1.20 (3H, d, J 6.4 Hz, 14-$H_3$), 1.33–1.47 (1H, m, 12-H), 1.61–1.81 (2H, m, 9-$H_2$), 1.90–2.01 (1H, m, 8-H), 2.37 (3H, s, 15-$H_3$), 2.38 (1H, dd, J 13.5 and 9.8 Hz, 4-H), 2.66–2.74 (2H, m, 4 and 11-H), 2.79–2.84 (1H, m, 10-H), 3.40 (1H, dd, J 9.2 and 3.2 Hz, 6-H), 3.55 (1H, d, J 11.6 Hz, 16-H), 3.55 (1H, d, J 19.5 Hz, $CH_AH_B$ furyl), 3.67 (1H, d, J 19.5 Hz, $CH_AH_B$ furyl), 3.74–3.92 (4H, m, 5, 7, 13, 16-H), 7.43 (1H, d, J 0.8 Hz, furyl), 7.95 (1H, d, J 0.8 Hz, furyl); $\delta_C$ ($CD_3OD$) 12.3 (C-17), 18.9 (C-15), 20.4 (C-14), 25.7 ($CH_2$ furyl), 33.1 (C-9), 41.7 (C-4), 41.9 (C-8), 43.8 (C-12), 56.9 (C-10), 61.4 (C-11), 66.5 (C-16), 70.4 (C-6), 70.8 (C-7), 71.7 (C-13), 77.0 (C-5), 130.8 (C-2), 134.8 (quat.), 137.1, 138.7 (quat.), 140.2, 154.0 (C-3), 190.1 (C-1); m/z 406 ($M^+$, 8%), 173 (100%); (Found: $M^+$, 406.1991. $C_{22}H_{30}O_7$ requires M, 406.1992).

EXAMPLE 6

E-5-(2-[3R,4R-Dihydroxy-5-(2S,3S-epoxy-5S-hydroxy-4S-methylhexyl)tetrahydropyran- 2S-yl]-1-methylethylidene))5,6-dihydro-4H-cyclopenta[b]furan-4-one a) 5-R,S(1-([3R,4R-Bistrimethyisilyloxy-5S(2S,3S-epoxy-5S-trimethylsilyloxy-4S-methylhexyl)tetrahydropyran-2S-yl]methyl)ethenyl))5,6-dihydro-4H-cyclopenta[b]furan-4-one Phosphorus tribromide (2.28 g, 8.38 mmol) in ether (8 ml) was added dropwise to 3-bromo-2-hydroxymethylfuran (3.71 g, 20.96 mmol) in ether (40 ml) at 5° C. After stirring for 1 h at room temperature excess sodium hydroxide solution (40%) was added. Extraction with ether, drying ($Na_2SO_4$) and evaporation to dryness under reduced pressure gave the crude bromomethyl furan (4.48 g) as a brown liquid. Di-iso-propylamine (0.16 ml) 1.2 mmol and t-butyl lithium (1.7M in hexane) (3.70 ml, 6.30 ml) were added dropwise sequentially to N-methoxy-N-methyl-6, 7, 13-O-tristrimethylsilyl monamide (3.61 g, 6.00 mmol) in THF (50 ml) maintaining the temperature below −65° C. After 1 h at −70° C. the crude 3-bromo-2-bromomethylfuran (4.48 g, 18.7 mmol) in THF (5 ml) was added dropwise. After stirring at room temperature for 72 h, water was added and the solution extracted with ethyl acetate. Drying ($Na_2SO_4$), evaporation to dryness under reduced pressure and purification by flash chromatography using hexane/ethyl acetate (4:1) as eluent gave the alkylated amide required (3.32 g) still containing some of the starting monamide. t-Butyl lithium (1.7M in hexane) (7.69 ml, 13.07 mmol) was added dropwise to this mixture maintaining the temperature below −70° C. After 2 h acetic acid (0.75 ml, 13.07 mmol) then water were added. Extraction with ethyl acetate, drying ($Na_2SO_4$), evaporation to dryness under reduced pressure and purification by flash chromatography using hexane/ethyl acetate (4:1) as eluent gave the title compounds (2.22 g, 82%) as a colourless oil; $\delta_H$ ($CD_3OD$) inter alia 0.10–0.16 (27H, m, 9×$SiCH_3$), 0.91 (3H, d, J 7.1 Hz, 17-$H_3$), 1.19 (3H, d, J 6.3 Hz, 14-$H_3$), 1.29–1.40 (1H, m, 12-H), 1.61–1.86 (3H, m, 8-H and 9-$H_2$), 1.95–2.05 (1H, m, 4-H), 2.38–2.44 (1H, m, 4-H), 2.69–2.72 (2H, m, 10 and 11-H), [5.00 (s), 5.01 (s), 5.06 (s) and 5.10 (s)] (2H, 15-$H_2$), 6.56 (1H, d, J 2.0 Hz, furyl-H); 7.71–7.73 (1H, m, furyl-H); m/z 622 ($M^+$, 4%), 169 (100%); (Found: $M^+$, 622.3192. $C_{13}H_{54}O_7Si_3$ requires M, 622.3177).

b) E-5-(2-[3R,4R-Bistrimethylsilyloxy-5S-(2S,3S-epoxy-5S-trimethylsilyloxy-4S-methylhexyl)tetrahydropyran-2S-yl]-(1-methylethylidene))-5,6-dihydro-4H-cyciopenta[b]furan-4-one Potassium t-butoxide (1.0M in THF) (2.65 ml, 2.65 mmol) was added dropwise to the above ketone (1.22 g, 1.96 mmol) in THF (40 ml) at −90° C. After 3 h at −90° C. acetic acid (0.30 ml, 5.30 mmol) in THF (3 ml) was added dropwise. After 1 h at −90° C. water was added and the products extracted with ethyl acetate. Drying ($Na_2SO_4$), evaporation to dryness under reduced pressure and purification by flash chromatography using hexane/ethyl acetate (5:1) as eluent gave the title compound (0.79 g, 65%) as a colourless oil; $\delta_H$ ($CD_3OD$) 0.10–0.20 (27H, m, 9×$SiCH_3$), 0.92 (3H, d, J 7.1 Hz, 17-$H_3$), 1.20 (3H, d, J 6.3 Hz, 14-$H_3$), 1.28–1.40 (1H, m, 12-H), 1.64–1.88 (3H, m, 8-H and 9-$H_2$), 2.26 (1H, dd, J 13.4 and 10.7 Hz, 4-H), 2.35 (3H, s, 15-$H_3$), 2.47–2.53 (1H, m, 4-H), 2.71–2.79 (2H, m, 10 and 11-H), 3.47–3.48 (3H, m, 6-H, $CH_AH_B$ furyl, and 16-H), 3.68 (1H, d, J 19.9 Hz. $CH_AH_B$ furyl), 6.58 (1H, d, J 2.0 Hz, furyl), 7.66 (1H, d, J 2.0 Hz, furyl); m/z 622 ($M^+$, 6%); (Found: $M^+$, 622.3178. $C_{37}H_{54}O_7Si_3$ requires M, 622.3179).

c) E-5-(2-[3R,4R-Dihydroxy-5S-(2S,3S-epoxy-5S-hydroxy- 4S-methylhexyl)tetrahydropyran- 2S-yl](1-methylethylidene)-5.6-dihydro-4H-cyclopenta[b]furan-4-one The above ketone (0.78 g, 1.25 mmol) and hydrochloric acid (0.4N) (7.5 ml, 3.0 mmol) in THF (37.5 ml) were stirred at room temperature for 2 min. Saturated sodium hydrogen carbonate solution was added. Extraction with ethyl acetate, drying ($Na_2SO_4$), evaporation to dryness under reduced pressure, purification by flash chromatography using 7% methanol in dichloromethane as eluent followed by recrystallisation from ethyl acetate/methanol/hexane gave the title compound (0.28 g, 56%) as white micro-needles (m.p. 166°–7° C.); $v_{max}$ (KBr) 3487, 2977, 2919, 2894, 2874. 1691, 1638, 1597, 1445, 1125, 1110 cm$^{-1}$; $\lambda_{max}$ (EtOH)

259.5 mm ($\epsilon_m$ 14 790); $\delta_H$ (CD$_3$OD) 0.94 (3H, d, J 7.1 Hz, 17-H$_3$), 1.20 (3H, d, J 6.4 Hz, 14-H$_3$), 1.33–1.46 (1H, m, 12-H), 1.62–1.80 (2H, m, 9-H$_2$), 1.88–1.97 (1H, m, 8-H), 2.35 (1H, dd, J 13.5 and 9.7 Hz, 4-H), 2.37 (3H, s, 15-H$_3$), 2.62–2.71 (2H, m, 4 and 11-H), 2.78–2.84 (1H, m, 10-H), 3.39 (1H, dd, J 3.0 and 9.5 Hz, 6-H), 3.53–3.65 (3H, m, CH$_A$H$_B$ furyl and 16-H), 3.71–3.91 (4H, m, 5, 7, 13 and 16-H), 6.58 (1H, d, J 2.0 Hz, furyl), 7.66 (1H, d, J 2.0 Hz, furyl); $\delta c$ (CD$_3$OD) 12.3 (C-17), 18.8 (C-14), 20.3 (C-15), 28.8 (CH$_2$ furyl), 32.8 (C-9), 41.2 (C-4), 41.5 (C-8), 43.4 (C-12), 56.7 (C-10), 61.2 (C-11), 66.3 (C-16), 70.0 (C-6), 70.5 (C-7), 71.4 (C-13), 76.5 (C-5), 105.9, 125.9 (q), 131.1 (q), 136.2 (q), 149.8, 150.6 (C-3), 188.6 (C-1); m/z 406 (M$^+$, 2%), 162 (100%); (Found: M$^+$, 406.2008. C$_{22}$H$_{10}$O$_7$ requires M, 406.1992).

EXAMPLE 7

E-2-(2-[3R,4R-Dihydroxy-5S-(2S,3S-epoxy-5S-hydroxy-4S-methylhexyl)tetrahydropyran-2S-yl)](1-methylethylidene))-5-methoxy-7-methylindan-1-one a) 2-R-S-(1-([3R,4R-Bistrimethylsilyloxy-5S-(2S,3S-epoxy-5S-trimethylsilyloxy- 4S-methylhexyl)tetrahydropyran-2S-yl]methyl)ethenyl)-5-methoxy- 7-methylindan-1-one Diisopropylamine (0.16 ml, 1.7 mmol) and t-butyl lithium (1.7M in hexane) (3.88 ml, 6.6 mmol) were added dropwise sequentially to N-methoxy-N-methyl-6, 7, 13-O-tris(trimethylsilyl) monamide (3.61 g, 6.0 mmol) in THF (30 ml) maintaining the temperature at −70° to −65° C. After 1 h at −70° C. 2-bromo-5-methoxy-3-methylbenzyl bromide (7.06 g, 24.0 mmol) in THF (10 ml) and lithium iodide (0.40 g, 2.99 mmol) were added and the solution stirred at RT for 96 h. Water was added and the products extracted with ethyl acetate. Drying (Na$_2$SO$_4$, evaporation to dryness and purification by flash chromatography gave the impure required alkylated products (3.048). t-Butyl lithium (1.7M in hexane) (5.50 ml, 9.33 mmol) was added dropwise to this product in THF (40 ml) maintaining the temperature below −70° C. After 2 h at −70° C. acetic acid (0.54 ml, 9.33 mmol) was added followed by water. Extraction with ethyl acetaste, drying (Na$_2$SO$_4$), evaporation to dryness under reduced pressure and purification by flash chromatography using hexane/ethyl acetate (4:1) as eluent gave the title compounds (1.68 g, 44%) as a colourless oil; $\delta_H$ (CDCl$_3$) inter alia 0.10–0.16 (27H, m, 9×SiCH$_3$), [0.89 (d, J 7.0 Hz) and 0.90 (d, J 7.0 Hz)] (3H, 17-H$_3$), 1.18 (3H, d, J 6.3 Hz, 14-H$_3$), 1.26–1.38 (1H, m, 12-H), 1.58–1.93 (3H, m, 9-H$_2$ and 8-H), 2.34–2.40 (1H, m, 4-H), 2.54 (3H, s, PhCH$_3$), 2.65–2.74 (2H, m, 10 and 11-H), 3.86 (3H, s, OCH$_3$), [4.95 (s), 5.07 (s), 5.07 (s), 5.09 (s)] (2H, 15-H), 6.68 (1H, s, aromatic), 6.83 (1H, br, s, aromatic); m/z 676 (M$^+$, 8%), 117 (100%); (Found: M$^+$, 676.3662. C$_{35}$H$_{60}$O$_7$Si$_3$ requires M, 676.3647).

b) E-2-(2-[3R,4R-Bistrimethyisilyloxy-5S(2S,3S-epoxy-5S-trimethylsilyloxy-4S-methylhexyl)tetrahydropyran-2S-yl]-(1-methylethylidene))-5-methoxy-7-methylindan-1-one Potassium t-butoxide (1.0M in THF) (2.80 ml, 2.80 mmol) was added to the above ketone (1.62 g, 2.40 mmol) in THF (25 ml) cooled to −70° C. After 2 h at −70° C. acetic acid (0.53 ml, 9.20 mmol) in ether (5 ml) was added and after 10 min at −70° C. water was added. Extraction with ethyl acetate, drying (Na$_2$SO$_4$), evaporation to dryness under reduced pressure and purification by flash chromatography using hexane/ethyl acetate (5:1) as eluent gave the title compound (0.71 g, 44%) as a colourless oil; $\delta_H$ (CDCl$_3$) 0.11–0.20 (27H, m, 9×SiCH$_3$), 0.92 (3H, d, J 7.0 Hz, 17-H$_3$), 1.19 (3H, d, J 6.3 Hz, 14-H$_3$), 14-H$_3$), 1.29–1.43 (1H, m, 12-H), 1.63–1.84 (3H, m, 9-H$_2$ and 8-H), 2.32 (1H, dd, J 13.5 and 10.5 Hz, 4-H), 2.37 (3H, s, 15-H$_3$) 2.56 (1H, d, J 13.5 Hz, 4-H), 2.59 (3H, s, PhCH$_3$) 2.72–2.80 (2H, m, 10 and 11-H), 3.49–3.60 (3H, m, 6 and 16-H, and CH$_A$H$_B$Ph), 3.69 (1H, d, J 20.3 Hz, CH$_A$H$_B$Ph), 3.83–3.96 (4H, m, 5, 7, 13 and 16-H), 3.85 (3H, s, OCH$_3$), 6.67 (1H, d, J 1.6 Hz, aromatic), 6.81 (1H, d, J 1.6 Hz, aromatic); m/z 676 (M$^+$, 8%), 73 (100%); (Found: M$^+$, 676.3650. C$_{35}$H$_{60}$O$_7$Si$_3$ requires M, 676.3647).

c) E-2-(2-[3R,4R-Dihydroxy-5S-(2S,3S-epoxy-5S-hydroxy- 4S-methylhexyl)tetrahydropyran- 2S-yl)](1-methylethylidene))-5-methoxy-7-methylindan- 1-one The above ketone (0.70 g, 1.04 mmol) and hydrochloric acid (0.4N) (6.00 ml, 2.40 mmol) in THF (30 ml) were stirred at room temperature for 2 min. Saturated sodium hydrogen carbonate solution was added and the solution extracted with ethyl acetate. Drying (Na$_2$SO$_4$), evaporation to dryness under reduced pressure and purification by flash chromatography using 8% methanol in dichloromethane as eluent gave the title compound (0.44 g, 92%) as a white foam: $\gamma_{max}$ (KBr) 3432, 2968, 2909, 1675, 1624, 1602, 1314, 1152 cm$^{-1}$; $\lambda_{max}$ (EtOH) 302.5 nm ($\epsilon_m$ 22791) and 243.0 nm ($\epsilon_m$ 8465); $\delta_H$ (CD$_3$OD) 0.94 (3H, d, J 7.1 Hz, 17-H$_3$), 1.20 (3H, d, J 6.4 Hz, 14-H$_3$,-H), 2.39 (3H, s. 15-H$_3$), 2.41 (1H, dd, J 13.8 and 9.7 Hz, 4-H), 2.59 (3H, s, CH$_3$), 2.66–2.74 (2H, m, 4 and 11-H), 2.81 (1H, dt, J 5.8 and 2.2 Hz, 10-H), 3.41 (1H, dd, J 9.1 and 3.1 Hz, 6-H), 3.54 (1H, dd, J 11.4 Hz, 16-H), 3.56 (1H, d, J 20.3 Hz, CH$_A$H$_B$Ph), 3.75 (1H, d, J 20.3 Hz, CH$_A$H$_B$Ph), 3.73–3.91 (4H, m, 5, 7, 13 and 16-H), 3.85 (3H, s, OCH$_3$) 6.66 (1H, d, J 1.6 Hz, aromatic); 6.82 (1H, d, J 1.6 Hz, aromatic); $\delta c$(CD$_3$OD) 12.2(C-12), 18.6 (CH$_3$ or C-15), 18.8 (CH$_3$ or C-15), (C-14), 32.3 (CH$_2$Ph), 41.5 (C-4), 41.7 (C-8), 43.6 (C-12), 55.9 (OCH$_3$),56.8 (C-10), 61.3 (C-11), 66.4 (C-16), 70.3 (C-6), 70.6 (C-7), 71.6 (C-13) 76.9 (C-5), 107.8, 117.4, 132.1 (C-2), 134.0(q), 141.7 (q) 153.9 (C-3), 165.6(q), 196.0 (C-1),m/z 460(M$^+$, 12%), 216 (100%); (Found: M$^+$, 460.2474. C$_{26}$H$_{36}$O$_7$ requires M, 460.2461).

EXAMPLE 8

E-5-(2-[3R,4R-Dihydroxy-5-(2S,3S-epoxy-5S-hydroxy-4S-methylhexyl)tetrahydropyran-2S-yl]-1-methylethylidene))-5-methylthioindan-1-one a) 5-R,S(1-([3R,4R-Bistrimethylsilyloxy-5S(2S,3S-epoxy- 5S-trimethylsilyloxy- 4S-methylhexyl)-tetrahydropyran-2S-yl]methyl)ethenyl)-5-methylthioindan-1-one Phosphorus tribromide (0.60 g, 2.20 mmol) in ether (5 ml) was added dropwise to 2-bromo-5-methylthiobenzyl alcohol (1.29 g, 5.53 mmol) in ether (20 ml) at 5° C. After stirring for 1 h at room temperature excess sodium hydroxide solution (40%) was added. Extraction with ether, drying (Na$_2$SO$_4$) and evaporation to dryness under reduced pressure gave the crude bromomethyl compound (1.70 g) as a brown liquid. Di-iso-propylamine (0.14 ml, 0.88 mmol) and t-butyllithium (1.7M in hexane) (3.58 ml, 6.09 ml) were added dropwise sequentially to N-methoxy-N-methyl-6, 7, 13-O-tristrimethylsilyl monamide (3.34 g, 5.54 mmol) in THF (40 ml) maintaining the temperature below −65° C. After 1 h at −70° C. the crude 2-bromo-5-methylthiobenzyl bromide (1.70 g, 5.44 mmol) in THF (10 ml) was added dropwise, followed by lithium iodide (0.40 g, 2.99 mmol). After stirring at room temperature for 60 h, water was added and the solution extracted with ethyl acetate. Drying (Na$_2$SO$_4$), evaporation to dryness under reduced pressure and purification by flash chromatography using hexane/ethyl acetate (4:1) as eluent gave the alkylated amide required (1.95 g) still containing some of the starting monamide.

t-Butyllithium (1.7M in hexane) (3.08 ml, 5.24 mmol) was added dropwise to this mixture maintaining the temperature below −70° C. After 2 h acetic acid (0.30 ml, 5.24 mmol) then water were added. Extraction with ethyl acetate, drying (Na$_2$SO$_4$), evaporation to dryness under reduced pressure and purification by flash chromatography using hexane/ethyl acetate (6:1) as eluent gave the title compounds (1.08 g, 67%) as a colourless oil; $\delta_H$ (CD$_3$OD) inter alia 0.10–0.16 (27H, m, 9×SiCH$_3$), [0.88 (d, J 6.8 Hz) and 0.90 (d, J 6.8 Hz)] (3H, 17-H$_3$), [1.17 (d, J 6.4 Hz) and 118(d,J 6.3 Hz)] (3H, 14-H$_3$), 1.26–1.40(1H, m, 12-H), 1.51–1.87 (3H, m, 8-H and 9-H$_2$), 1.85–2.07 (1H, m, 4-H), 2.38–2.45 (3H, m, 10, 11 and 4-H), [2.54 (s) and (2.55 (s)] (3H, SCH$_3$), [4.97 (s), 5.04 (s), and 5.09 (s)] (2H, 15-H$_2$), 7.27–7.28 (1H, m, 6'-H), [7.35(s) and 7.37 (s)], [1H, 4'-H), 7.61 (1H, d, J 8.1 Hz, 7'-H); m/z 679 (M$^+$, 7%), 117 (100%); (Found: M$^+$, 679.355. C$_{34}$H$_{59}$O$_6$Si$_3$S requires M, 679.3340).

b) E-5-(2-(3R,4R-Bistrimethylsilyloxy-5S-(2S,3S-epoxy-5S-trimethylsilyloxy-4S-methylhexyl)tetrahydropyran-2S-yl]-(1-methylethylidene))- 5-methylthioindan-1 one Potassium t-butoxide (1.0M in THF) (1.75 ml, 1.75 mmol) was added dropwise to the above ketone (1.08 g, 1.59 mmol) in THF (40 ml) at −0° C. After 2 h at −90° C. acetic acid (0.29 ml, 5.08 mmol) in THF (2 ml) was added dropwise. After 0.5 h at −90° C. water was added and the products extracted with ethyl acetate. Drying (Na$_2$SO$_4$), evaporation to dryness under reduced pressure and purification by flash chromatography using hexane/ethyl acetate (7:1) as eluent gave the title compound (0.85 g, 79%) as a colourless oil; $\delta_H$ (CD$_3$OD) 0.10–0.20 (27H, m, 9×SiCH$_3$), 0.93 ( 3H, d, J 7.0 Hz, 17-H$_3$), 1.20 (3H, d, J 6.3 Hz, 14-H$_3$), 1.28–1.43 (1H, m, 12-H), 1.64–1.89 (3H, m, 8-H and 9-H$_2$),2.37 (1H, dd, J 13.4 and 10.6 Hz, 4-H),2.41 (3H, s, 15-H$_3$), 2.54 (3H, s, SCH$_3$),2.71–2.82 (3H, m, 4, 10 and 11-H), 3.51 (1H, d, J 11.5 Hz, 16-H),3.57 (1H, J 8.9 and 2.4 Hz, 6-H), 3.63 (1H, d, J 20.3 Hz, CH$_A$H$_B$ phenyl), 3.76 (1H, d, J 20.4 Hz, CH$_A$H$_B$ phenyl), 7.24 (1H, dd, J 8.2 and 1.3 Hz, 6'-H), 7.34 (1H, d, J 1.3 Hz, 4'-H), 7.60 (1H, d, J 8.2 Hz, 7'-H); m/z 679 (M$^+$, 8%); (Found: M$^+$, 679.3349. C$_{34}$H$_{59}$O$_6$Si$_3$S requires M, 679.3340).

c) E-5-(2-[3R,4R-Dihydroxy-5S-(2S,3S-epoxy-5S-hydroxy- 4S-methylhexyl)tetrahydropyran- 2S-yl]-(1-methylethylidene)-5-methylthioindan-1-one The above ketone (0.84 g, 1.28 mmol) and hydrochloric acid (0.4N) (7.43 ml, 2.97 mmol) in THF (40.0 ml) were stirred at room temperature for 2 min. Saturated sodium hydrogen carbonate solution was added. Extraction with ethyl acetate, drying (Na$_2$SO$_4$), evaporation to dryness under reduced pressure, purification by flash chromatography using 7% methanol in dichloromethane as eluent followed by recrystallisation from ethyl acetate/methanol/hexane gave the title compound (0.43 g, 75%) as white micro-needles (m.p. 156°–7° C.); $\nu_{max}$ (KBr) 3424, 2985, 2963, 2947, 2901, 2863, 1671, 1613, 1590, 1323, 1115, 1056, 773 cm$^{-1}$; $\lambda_{max}$ (EtOH) 333.5 nm ($\epsilon_m$ 24,634); $\delta_H$ (CD$_3$OD) 0.95 (3H, d, J 7.1 Hz, 17-H$_3$), 1.20 (3H, d, J 6.4 Hz, 14-H$_3$), 1.33–1.46 (1H, m, 12-H), 1.62–1.80 (2H, m, 9-H$_2$), 1.88–1.97 (1H, m. 8-H), 2.43 ( 3H, s, 15-H$_3$), 2.45 (1H, dd, J 13.4 and 9.7 Hz. 4-H), 2.55 (3H, s, SCH$_3$), 2.70–2.84 (3H, m, 4,10 and 11-H), 3.42 (1H, dd, J 3.2 and 9.3 Hz, 6-H), 3.55 (1H, d, J 11.6 Hz, 16-H), 3.67 (1H, d, J 20.5 Hz, CH$_A$H$_B$Ph), 3.71–3.92 (5H, m, 5, 7, CH$_A$H$_B$Ph. 13 and 16-H), 7.24 (1H, dd, J 8.2 and 1.3 Hz. 6'-H), 7.35 (1H, d, J 1.3 Hz, 4'-H), 7.60(1H, d, J 8.2 Hz, 7'-H); $\delta_C$(CDCl$_3$) 12.6(C-17), 14.9(SCH$_3$),18.7 (C-15), 20.7 (C-14), 31.7 (CH$_2$ phenyl), 32.1 (C-9), 39.6 (C-8), 40.7 (C-4), 42.6 (C-12), 55.5 (C-10), 61.3 (C-11), 65.5 (C-16), 69.1 (C-6), 70.1 (C-7), 71.1 (C-13), 75.6 (C-5), 121.5, 123.9, 124.5, 132.1 (q), 137.1 (q), 146.9 (q), 149.1 (q), 150.6 (C-3), 193.6 (C-1); m/z 462 (M$^+$, 1%), 218 (100%); (Found: M$^+$, 462.2079. C$_{25}$H$_{34}$O$_6$S requires M, 462.2076).

EXAMPLE 9

E-5-(2-[3R,4R-Dihydroxy-5-(2S,3S-epoxy-5S-hydroxy-4S-methylhexyl)tetrahydropyran-2S-yl]-1-methylethylidene))-5-methylsulphinylindan-1-one m-Chloroperoxybenzoic acid (0.074 g, 0.43 mmol) and Example 8 (0.18 g, 0.39 mmol) in dichloromethane (10 ml) and saturated sodium hydrogen carbonate (aq) (5 ml) were stirred at 0° C. for 1 h. Extraction with dichloromethane, drying (Na$_2$SO$_4$), evaporation to dryness under reduced pressure and purification by flash chromatography using 7–9% methanol in dichloromethane as eluent gave the title compound (0.092 g, 49%) as a white foam; $\nu_{max}$ (KBr) 3409, 2968, 2874, 1687, 1622, 1600, 1418, 1107, 1060 cm$^{-1}$; $\lambda_{max}$ (EtOH) 293.5 nm ($\epsilon_m$ 20,860); $\delta_H$ (CD$_3$OD) 0.95 (3H, d, J 7.1 Hz, 17-H$_3$), 1.20 (3H, d, J 6.4 Hz, 14-H$_3$), 1.33–1.44 (1H, m, 12-H), 1.63–1.81 ( 2H, m, 9-H$_2$), 1.86–2.01 (1H, m, 8-H), 2.46 (3H, s, 15-H$_3$), 2.50 (1H, dd, J 13.6 and 9.7 Hz, 4-H), 2.70–2.84 (3H, m, 4, 10 and 11-H), 2.84 (3H, s, SOCH$_3$), 3.43 (1H, dd, J 9.3 and 3.0 Hz, 6-H), 3.54 (1H, d, J 11.7 Hz, 16-H), 3.69–3.97 (6H, m, 5, 7, 13 and 16-H, and CH$_2$Ph), 7.68 (1H, d, J 7.8 Hz, aromatic), 7.86–8.07 (2H, m, aromatic); $\delta_C$ (CD$_3$OD) 12.2 (C-17), 19.3 (C-15), 20.3 (C-14), 33.0 (CH$_2$P), 33.1 (C-9), 41.8 (C-8), 41.9 (C-4), 43.6 (C-12), 43.7 (SOCH$_3$), 56.8 (C-10), 61.2 (C-11), 66.4 (C-16), 70.3 (C-6), 70.6 (C-7), 71.6 (C-13), 76.9 (C-5), 122.6, 123.5, 125.4, 133.0 (q), 143.4 (q), 150.9 (q), 152.3 (q), 155.2 (C-3), 194.9 (C-1); m/z (F.A.B.) (thioglycerol) 479 (MH$^+$, 45%).

EXAMPLE 10

E-5-(2-[3R,4R-Dihydroxy-5-(2S,3S-epoxy-5S-hydroxy-4S-methylhexyltetrahydropyran-2S-yl]-1-methylethylidene))-5-methylsulphinylindan-1-one m-Chloroperoxybenzoic acid (0.115 g, 0.67 mmol) and Example 8 (0.14 g, 0.30 mmol) in dichloromethane (10 ml) and saturated sodium hydrogen carbonate solution (9 q.) (10 ml) were stirred at 0° C. for 3 h. Extraction with dichloromethane, drying (Na$_2$SO$_4$) and evaporation to dryness under reduced pressure gave on recrystallisation from methanol/ethyl acetate the title compound (0.050 g. 33%) as white micro-needles (m.p. 185°–6° C.); $\nu_{max}$ (KBr) 3463, 2975, 2889, 1687, 1623, 1604, 1304, 1135 cm$^{-1}$; $\nu_{max}$ (EtOH) 291.0 nm ($\epsilon_m$ 16.550) and 256.0 nm ($\epsilon_m$ 13.505); $\delta_H$ [(CD$_3$)$_2$CO] 0.92 (3H, d, J 7.0 Hz, 17-H$_3$), 1.20 (3H, d, J 6.4 Hz, 14-H$_3$), 1.32–1.43 ( 1H, m, 12-H), 1.60–1.83 (2H, m, 9-H$_2$), 1.36–2.01 (1H, m, 8-H),2.47 (3H, s, 15-H$_3$), 2.51 (1H, dd, J 13.4 and 9.4 Hz, 4-H), 2.71 (1H, dd, J 7.4 and 2.1 Hz, 11-H), 2.76–2.84 (2H, m, 4 and 10-H), 2.85 (3H, s, SO$_2$CH$_3$), 3.53 (1H, d, J 11.3 Hz, 16-H), 3.75–4.08 (7H, m, CH$_2$Ph, 6, 16, 5, 7, and 13-H), 7.91 (1H, d, J 8.0 Hz, 7'-H), 7.99 (1H, d, J 8.0 Hz, 6'-H), 8.14 (1H, s, 4'-H); m/z (D.C.I.) (NH$_3$) 512 (MNH$_4^+$, 20%), 495 (MH$^+$, 52%).

EXAMPLE 11

E-2-(2-[3R,4R-Dihydroxy-5S-(2S,3S-epoxy-5S-hydroxy-4S-methyl)tetrahydropyran-2S-yl)]-(1-methylethylidene))-6-methoxyindan-1-one a) E-2-(2-[3R,4R-Bistrimethyisilyloxy-5S-(2S,3S-epoxy-5S-trimethylsilyloxy-4S-methylhexyl)tetrahydropyran-2S-yl]-(1-methylethylidene))-6-methoxyindan-1-one Diisopropylamine (0.16 ml, 1.20 mmol) and t-butyllithium (1.7M in hexane) (3.88 ml, 6.6 mmol) were added dropwise sequentially to N-methoxy-N-methyl-6, 7, 13-O-tris-(trimethylsilyl)monamide (3.61 g, 6.00 mmol) in THF (30 ml) maintaining the temperature below −65° C. After 1 h at −70° C., 2-bromo-4-methoxybenzyl bromide (3.36 g, 12.0 mmol) and lithium iodide (0.40 g, 3.63 mmol) were added and the mixture heated to reflux for 60 h. The products were poured into water and extracted with ethyl acetate, dried ($Na_2SO_4$) and evaporated to dryness under reduced pressure. Removal of the excess benzyl bromide present by flash chromatography using hexane/ethyl acetate (4:1) as eluent gave the required alkylated amides contaminated with the starting amide. This mixture was treated with t-butyllithium (1.7M in hexane) (2.55 ml, 4.34 mmol) in THF (20 ml) at −70° C. for 2 h. Addition of water, extraction with ethyl acetate, drying ($Na_2SO_4$), evaporation to dryness under reduced pressure and purification by flash chromatography using hexane/ethyl acetate (5:1) as eluent gave a mixture of the required deconjugated ketones (0.61 g). This mixture was treated with potassium t-butoxide (1.0M in THF) (1.25 ml, 1.25 mmol) in THF (10 ml) at −90° C. for 2 h. Acetic acid (0.12 ml, 2.01 mmol) then water were added. Extraction with ethyl acetate, drying ($Na_2SO_4$), evaporation to dryness under reduced pressure and purification by flash chromatography using hexane/ethyl acetate (5:1) as eluent gave the title compound (0.53 g, 14%) as a white foam: $\delta H$ ($CD_3OD$) 0.10–0.17 (27H, m, 9×$SiCH_3$), 0.92 (3H, d, J 7.0 Hz, 17-$H_3$), 1.19 (3H, d, J 6.3 Hz, 14-$H_3$), 1.33–1.44 (1H, m, 12-H), 1.69–1.88 (3H, m, 9-$H_2$ and 8-H), 2.36 (1H, dd, J 13.4 and 10.6 Hz, 4-H), 2.42 (3H, s, 15-$H_3$), 2.60 (1H, d, J 13.4 Hz, 4-H), 2.72–2.80 (2H, m, 10 and 11-H), 3.50–3.94 (8H, m, 5, 7, 13, 6-H, 16-$H_2$ and $CH_2Ph$), 3.83 (3H, s, $OCH_3$), 7.17–7.21 (2H, m, phenyl), 7.42 (1H, d, J 8.8 Hz, phenyl): m/z 662 ($M^+$, 8%), 117 (100%); (Found: $M^+$, 662.3448. $C_{34}H_{58}O_7Si_3$ requires M, 662.3490).

b) E-2-(2-[3R,4R-Dihydroxy-5S-(2S,3S-epoxy-5S-hydroxy- 4S-methylhexyl)tetrahydropyran- 2S-yl)]-(1-methylethylidene))-6-methoxyindan-1-one The above ketone (0.52 g, 0.84 mmol) and hydrochloric acid (0.4N) (5.04 ml, 1.26 mmol) in THF (25 ml) were stirred at room temperature for 2 min. Addition of saturated sodium hydrogen carbonate solution, extraction with ethyl acetate, drying ($Na_2SO_4$), evaporation to dryness under reduced pressure, and purification by flash chromatography using 7% methanol in dichloromethane as eluent gave the title compound (0.27 g, 80%) as a white foam: $\nu_{max}$ (KBr) 3428, 2969, 2901, 1675, 1615, 1490, 1297, 1106, 1053, 1028, 779 $cm^{-1}$; $\lambda_{max}$ (EtOH) 333.0 nm ($\epsilon_m$ 3,798) and 281.5 nm ($\epsilon_m$ 16,200); $\delta_H$ ($CD_3OD$) 0.94 (3H, d, J 7.1 Hz, 17-$H_3$), 1.19 (3H, d, J 6.4 Hz, 14-$H_3$), 1.33–1.47 (1H, m, 12-H), 1.62–1.81 (2H, m, 9-$H_2$), 1.87–1.97 (1H, m, 8-H), 2.44 (3H, s, 15-$H_3$), 2.45 (1H, dd, J 13.5 and 9.7 Hz, 4-H), 2.70–2.84 (3H, m, 4, 10 and 11-H), 3.42 (1H, dd, J 9.3 and 3.0 Hz, 6-H), 3.54 (1H, d, J 11.8 Hz, 16-H), 3.62–3.92 (6H, m, 5, 7, 13, 16-H and $CH_2Ph$), 3.84 (3H, s, $OCH_3$), 7.17–7.20 (2H, m, phenyl), 7.41 (1H, d, J 9.3 Hz, phenyl); $\delta_C$ ($CD_3OD$) 10.8 (C-17), 17.7 (C-15), 18.9 (C-14), 30.8 ($CH_2Ph$), 31.6 (C-9), 40.3 (C-8), 40.3 (C-4), 42.3 (C-12), 54.5 ($OCH_3$), 55.4 (C-10), 60.0 (C-11), 65.0 (C-16), 68.9 (C-6), 69.3 (C-7), 70.2 (C-13), 75.5 (C-15), 104.9, 122.6, 126.6, 132.7 (q), 140.8 (q), 141.3 (q), 151.9 (q), 159.3 (C-3), 194.6 (C-1); m/z 446 ($M^+$, 4%); (Found: $M^+$, 446.2308. $C_{25}H_{34}O_7$ requires M, 446.2305).

EXAMPLE 12

E-2-(2-[3R,4R-Dihydroxy-5S-(2S,3S-epoxy-5S-hydroxy-4S-methylhexyl)tetrahydropyran-2S-yl)]-(1-methyl-ethylidene))-5-hydroxyindan-1-one a) 2-Bromo-5-t-butyldimethylsilyloxybenzyl bromide 4-Bromo-3-methylphenol( 4.49 g, 24.0 mmol), t-butyldimethylsilyl chloride (5.43 g, 36.0 mmol) and imidazole (4.90 g, 22.0 mmol) in N,N-dimethylformamide (30 ml) were stirred at room temperature for 16 h. Water (100 ml) was added and the products extracted with ethyl acetate. Drying ($MGSO_4$), evaporation to dryness under reduced pressure and purification by flash chromatography using hexane as eluent gave the crude silylated phenol (4.16 g, 57%), to this crude product (4.16 g, 13.77 mmol) was added N-Bromosuccinimide (2.70 g, 15.15 mmol) and carbon tetrachloride (100 ml). The mixture was heated to reflux over a 150 W light bulb for 2 h. Cooling to 5° C., filtration, evaporation of the filtrate to dryness under reduced pressure and purification by flash chromatography using hexane as eluent gave the title compound as a colourless oil: $\delta_H$ ($CDCl_3$) 0.20 [6H, s, $Si(CH_3)_2$], 0.97 (9H, s, $^tbu$), 4.50 (2H, s, $CH_2Br$), 6.63 (1H, dd, J 2.9 and 8.5 Hz, 4-H), 6.91 (1H, d, J 2.9 Hz, 5-H), 7.37 (1H, d, J 8.5 Hz, 3-H); m/z (E.I.) 382 ($M^+$, 5%), 380 ($M^+$, 10%), 378 ($M^+$, 5%); (Found: $M^+$, 377.9642. $C_{13}H_{20}Br_2OS$; requires M, 377.9652).

b) E-2-(2-[3R,4R-Bistrimethyisilyloxy-5S-(2S,3S-epoxy-5S-trimethylsilyloxy-4S-methylhexyl)tetrahydropyran-3S-yl]-(1-methylethylidene))-5-t-butyldimethylsilyloxyindan-1-one Diisopropylamine (0.16 ml, 1.16 mmol)and t-butyllithium (1.7M in hexane (3.88 ml, 6.60 mmol) were added dropwise sequentially to N-methoxy-N-methyl-6,7,13-O-tris(trimethylsilyl)monamide (3.60 g, 6.00 mmol) in THF (30 ml) maintaining the temperature below −65° C. After 1 h at −70° C., 2-bromo-5-t-butyldimetyhylsilyloxybenzyl bromide (3.01 g, 7.90 mmol) and lithium iodide (0.20 g, 1.31 mmol) were added and the mixture heated to reflux for 60 h. The products were poured into water and extracted with ethyl acetate, dried ($Na_2SO_4$) and evaporated to dryness under reduced pressure. Removal of the excess benzyl bromide present by flash chromatography using hexane/ ethyl acetate (6:1) as eluent gave a complex mixture (2.30 g). This mixture was treated with t-butyllithium (1.7M in hexane) (3.30 ml, 5.61 mmol) in THF (20 ml) at −70° C. for 2 h. Addition of water, extraction with ethyl acetate, drying ($Na_2SO_4$), evaporation to dryness under reduced pressure and purification by flash chromatography using hexane/ethyl acetate (7:1) as eluent gave a complex mixture containing the required deconjugated ketones (1.03 g). This mixture was treated with potassium t-butoxide (0.20 g, 1.60 mmol) in THF (10 ml) at −70° C. for 2 h. Acetic acid (0.16 ml, 2.8 mmol) then water added. Extraction with ethyl acetate, drying ($Na_2SO_4$), evaporation to dryness under reduced pressure and purification by flash chromatography using hexane/ethyl acetate (8:1) as eluent gave the title compound (0.63 g, 14%) as a white foam; $\delta_H$ ($CD_3OD$) 0.10–0.27

(33H, m, 11×SiCH$_3$), 0.92 (3H, d, J 7.0 Hz, 17-H$_3$), 1.01 (9H, s, $^t$Bu), 1.20 (3H, d, J 6.3 Hz, 14-H$_3$), 1.28–1.42 (1H, m, 12-H), 1.67–1.83 (3H, m, 9-H$_2$ and 8-H), 2.36 (1H, dd, J 13.4 and 10.5 Hz, 4-H), 2.40 (3H, s, 15-H$_3$), 2.58 (1H, d, J 13.4 Hz, 4-H), 2.72–2.82 (2H, m, 10 and 11-H), 3.50–3.95 (8H, m, 5,7,13, 16-H, 16-H$_2$ and CH$_2$Ph), 6.87 (1H, dd, J 8.3 and 2.0 Hz, phenyl), 6.93 (1H, d, J 2.0 Hz, phenyl), 7.63 (1H, d, J 8.3 Hz, phenyl); m/z 762 (M$^+$, 13%), 173 (100%); (Found: M$^+$, 762.4209. C$_{39}$H$_{70}$O$_7$Si$_4$ requires M, 762.4199).

c) E-2-(2-[3R,4R-Dihydroxy-5S-(2S,3S-epoxy-5S-hydroxy- 4S-methylhexyl)tetrahydropyran- 2S-yl)]-(1-methylethylidene))-5-hydroxyindan-1-one The above ketone (0.62 g, 0.81 mmol) was treated with tetra-n-butylammonium fluoride in THF (15 ml) at 5° C. for 10 mins. Addition of a pH 7 buffer solution (20 ml), extraction with ethyl acetate, drying (Na$_2$SO$_4$) evaporation to dryness under reduced pressure, and purification by flash chromatography using 10% methanol in dichloromethane as eluent gave the title compound (0.34 g, 97%) as a white foam: $\nu_{max}$ (KBr) 3423, 2966, 2966, 2927, 1669, 1623, 1585, 1304, 1266, 1093 cm$^{-1}$; $\lambda_{max}$ (EtOH) 312 nm ($\epsilon_m$ 16,596) and 293.5 nm (sh) ($\epsilon_m$ 14,072); $\delta_H$ CD$_3$OD) 0.94 (3H, d, J 7.1 Hz, 17-H$_3$), 1.19 (3H, d, J 6.4 Hz, 14-H$_3$), 1.33–1.44 (1H, m, 12-H), 1.61–1.83 ( 2H, m, 9-H$_2$), 1.87–1.97 (1H, m, 8-H), 2.40 (2H, s, 15-H$_3$), 2.45 (1H, dd, J 13.6 and 9.6 Hz, 4-H), 2.72–2.84 (3H, m, 4,10 and 11-H), 3.40 (1H, dd, J 9.3 and 3.0 Hz, 6-H), 3.53 (1H, d, J 11.6 Hz, 16-H), 3.50–3.94 (6H, m, 5,7,13, 16-H) and CH$_2$Ph), 6.77 (1H, dd, J 2.1, 8.3 Hz, phenyl), 6.80 (1H, d, J 2.1 Hz, phenyl), (1H, d, J 8.3 Hz, phenyl); $\delta_C$ (CD$_3$OD) 12.2 (C-17), 18.7 (C-14), 20.3 (C-15), 32.9 (CH$_2$Ph), 33.0 (C-9), 41.6 (C-4), 41.7 (C-8), 43.6(C-12),56.8 (C-10), 61.3 (C-11), 66.4 (C-16), 70.3 (C-6), 70.7 (C-7), 71.6 (C-13), 76.9 (C-5), 112.3, 116.8, 126.6, 133.5 (q), 133.6 (q), 151.2 (q), 153.3 (q), 164.9 (q), 195.1 (C-1), m/z 432 (M$^+$, 4%): (Found: M$^+$, 432.2158. C$_{24}$H$_{32}$O$_7$ requires M, 432.2148).

EXAMPLE 13

E-2-(2-[3R,4R-Dihydroxy-5S-
(2S,3S-epoxy-5S-hydroxy-
4S-methylhexyl)-tetrahydropyran-
2S-yl)]-(1-methylethylidene))-6-hydroxyindan-1-one a) 2-Bromo-4-t-butyldimethylsilyloxybenzyl bromide 3-Bromo-4-methylphenol( 25.0 g, 0.134 mol) and aluminum chloride (36.11 g, 0.27 mol) were heated to 127° C. for 2 h. Ice was added, the solution extracted with ethyl acetate, dried (Na$_2$SO$_4$) and evaporated to dryness under reduced pressure. N,N-Dimethyl formamide (150 ml), t-butyl-dimethylchlorosilane (25.0 g, 165 mmol) and imidazole (22.6 g, 33.2 mmol) were added and the solution stirred at room temperature for 16 h. The products were partitioned between water and ethyl acetate, the organic layer separated, dried (Na$_2$SO$_4$) and evaporated to dryness under reduced pressure. Purification by flash chromatography using hexane as eluent gave impure 1-bromo-2-methyl-5-t-butyldimethylsilyloxybenzene (22.0 g). Carbon tetrachloride (125 ml) and N-bromosuccinimide (10.80 g, 66.6 mmol) were added and the solution heated to reflux over a 150 W light bulb for 2 h. The solution was cooled to 5° C., filtered and evaporated to dryness under reduced pressure. Purification by flash chromatography using hexane as eluent gave the title compound (12.64 g, 21%) as a white solid; $\delta_H$ (CDCl$_3$) 0.21 (6H, s, Si(CH$_3$)$_2$), 0.97 (9H, s, t-Bu), 4.59 (2H, s, CH$_2$Br), 6.76 (1H, dd, J 8.3 and 2.4 Hz, 4-H), 7.07 (1H, d, J 2.4 Hz, 6-H), 7.30 (1H, d, J 8.4 Hz, 3-H): m/z (E.I.) 382 (M$^+$, 2%), 380 (M$^+$, 4%), 378 (M$^+$, 2%), 299 (100%): (Found: M$^-$ 377.9647). C$_{13}$H$_{20}$OBr$_2$Si requires M, 377.9650).

b) E-2-(2-[3R,4R-Bistrimethylsilyloxy-5S-(2S,3S-epoxy-5S-trimethyl-silyloxy- 4S-methylhexyl)tetrahydropyran-2S-yl]-(1-methylethylidene))-6-t-butyldimethylsilyloxyindan-1-one Diisopropylamine (0.16 ml, 1.16 mmol) and t-butyllithium (1.7M in hexane) (3.88 ml, 6.60 mmol) were added dropwise sequentially to N-methoxy-N-methyl-6,7,13-O-tris(trimethylsilyl)monamide (3.60 g, 6.00 mmol) in THF (30 ml) maintaining the temperature below −65° C. After 1 h at −70° C., 2-bromo-4-t-butyldimethylsilyloxybenzyl bromide (5.32 g, 13.9 mmol) and lithium iodide (0.20 g, 1.31 mmol) were added and the mixture heated to reflux for 60 h. The products were poured into water and extracted with ethyl acetate, dried (Na$_2$SO$_4$) and evaporated to dryness under reduced pressure. Removal of the excess benzyl bromide present by flash chromatography using hexane/ ethyl acetate (6:1) as eluent gave a complex mixture (2.43 g). This mixture was treated with t-butyllithium (1.7M in hexane) (3.30 ml, 5.61 mmol) in THF (20 ml) at −70° C. for 2 h. Addition of water, extraction with ethyl acetate, drying (Na$_2$SO$_4$), evaporation to dryness under reduced pressure and purification by flash chromatography using hexane/ethyl acetate (7:1) as eluent gave a complex mixture containing the required deconjugated ketones (0.69 g). This mixture was treated with potassium t-butoxide (0.121 g, 0.99 mmol) in THF (10 ml) at −70° C. for 2 h. Acetic acid (0.15 ml, 2.62 mmol) then water were added. Extraction with ethyl acetate, drying (Na$_2$SO$_4$), evaporation to dryness under reduced pressure and purification by flash chromatography using hexane/ethyl acetate (8:1) as eluent gave the title compound (0.53 g, 12%) as a white foam; $\delta_H$ (CD$_3$OD) 0.10–0.27 (33H, m, 11×SiCH$_3$), 0.92 (3H, d, J7.0 Hz, 17-H$_3$), 1.01 (9H, s, $^t$Bu), 1.20 (3H, d, J 6.3 Hz, 14-H$_3$), 1.28–1.42 (1H, m, 12-H), 1.67–1.83 (3H, m, 9-H$_2$ and 8-H), 2.36(1H, dd, J13.4 and 10.5 Hz, 4-H),242 (3H, s, 15-H$_3$), 258(1H, d, J 13.4 Hz, 4-H), 2.72–2.82 (2H, m, 10 and 11-H), 3.50–3.95 (8H, m, 5,7,13, 16-H, 16-H$_2$ and CH$_2$Ph), 7.11 (1H, dd, J 8.3 and 2.4 Hz, phenyl), 7.14 (1H, d, J 2.4 Hz phenyl), 7.56 (1H, d, J 8.3 Hz, phenyl); m/z 762 (M$^+$, 18%), 73 (100%); (Found: M$^+$, 762.4202. C$_{39}$H$_{70}$O$_7$Si$_4$ requires M, 762.4199).

c) E-2-(2-[3R,4R-Dihydroxy-5S(2S,3S-epoxy-5S-hydroxy-4S-methylhexyl)tetrahydropyran- 2S-yl)]-(1-methylethylidene))-6-hydroxyindan-1-one The above ketone (0.52 g, 0.68 mmol) was treated with tetra-n-butylammonium fluoride trihydrate (0.86 g, 2.72 mmol) in THF (15 ml) at 5° C. for 10 mins. Addition of a pH 7 buffer solution (20 ml), extraction with ethyl acetate, drying (Na$_2$SO$_4$) evaporation to dryness under reduced pressure, and purification by flash chromatography using 10% methanol in dichloromethane as eluent gave the title compound (0.24 g, 82%) as a white foam: $\nu_{max}$ (KBr) 3430, 2966, 2927, 1669, 1615, 1465, 1296, 1106, 1052 cm$^{-1}$; $\lambda_{max}$ (EtOH) 341.5 nm ($\epsilon_m$ 3640) and 281.5 nm ($\epsilon_m$ 18949): $\delta_H$ (CD$_3$OD) 0.94 (3H, d, J 7.1 Hz, 17-H$_3$), 1.19 (3H, d, J 6.4 Hz, 14-H$_3$), 1.33–1.44 (1H, m, 12-H), 1.61–1.83 ( 2H, m, 9-H$_2$), 1.87–1.97 (1H, m, 8-H), 2.43 (2H, s, 15-H$_3$), 2.45 (1H, dd, J 13.6 and 9.6 Hz, 4-H), 2.72–2.84 (3H, m, 4,10 and 11-H), 3.40 (1H, dd, J 9.3 and 3.0 Hz, 6-H), 3.53 ( 1H, d, J 11.6 Hz, 16-H), 3.50–3.94 (6H, m, 5,7,13, 16-H and CH$_2$Ph), 7.05–7.09 (2H, m, phenyl), 7.34 (1H, d, J 8.3 Hz, phenyl); $\delta_C$ (CD$_3$OD) 12.2 (C-17), 19.0 (C-14), 20.3 (C-15), 32.1 (CH$_2$Ph), 33.0 (C-9), 41.6 (C-4), 41.7 (C-8), 43.6 (C-12), 56.8 (C-10), 61.3 (C-11), 66.4 (C-16), 70.3 (C-6), 70.7 (C-7), 71.6 (C-13), 76.9 (C-5), 109.1, 124.0, 127.9, 134.2 (q), 141.4 (q), 142.3 (q), 153.0 (q), 158.1 (q), 193.4

(C-1), m/z 432 (M+, 18%); (Found: M+, 432.2150. C24H32O7 requires M, 32.2148).

EXAMPLE 14

E-6-(2-[3R,4R-Dihydroxy-5S(2S,3S-epoxy-5S-hydroxy-4S-methylhexyl)-tetrahydropyran-2S-yl)]-(1-methylethylidene))-5,6-dihydro-H-cyclopenta-[b]pyridin-7-one a) E-6-(2-[3R,4R-Bistrimethylsilyloxy-5S-(2S3S-epoxy-5S-trimethylsilyloxy-S-methylhexyl)tetrahydropyran-2S-yl]-(1-methylethyl-idene))-5,6-dihydro-H-cyclopenta[b]pyridin-7-one Diisopropylamine (0.16 ml, 1.20 mmol) and t-buryl-lithium (1.7M in hexane) (3.88 ml, 6.6 mmol) were added dropwise sequentially to N-methoxy-N-methyl-6,7,13-O-tris-(trimethylsilyl)monamide (3.61 g, 6.00 mmol) in THF (30 ml) maintaining the temperature below −65° C. After 1 h at −70° C., 2-bromo-3-bromomethylpyridine (5.66 g, 22.2 mmol) and lithium iodide (0.40 g, 3.63 mmol) were added and the mixture heated to reflux for 60 h. The products were poured into water and extracted with ethyl acetate, dried (Na2SO4) and evaporated to dryness under reduced pressure. Removal of the excess benzyl bromide present by flash chromatography using hexane/ethyl acetate (3:1) as eluent gave the required alkylated amides (2.36 g) contaminated with the starting amide. This mixture was treated with t-butyllithium (1.7M in hexane) (3.95 ml, 6.72 mmol) in THF (20 ml) at −70° C. for 2 h. Addition of water, extraction with ethyl acetate, drying (Na2SO4), evaporation to dryness under reduced pressure and purification by flash chromatography using hexane/ethyl acetate (3:1) as eluent gave a mixture of the required deconjugated ketones (1.23 g). This mixture was treated with potassium t-butoxide (1.0M in THF) (2.33 ml, 2.33 mmol) in THF (10 ml) at −90° C. for 2 h. Acetic acid (0.23 ml, 3.83 mmol) then water were added. Extraction with ethyl acetate, drying (Na2SO4), evaporation to dryness under reduced pressure and purification by flash chromatography using hexane/ethyl acetate (2:1) as eluent gave the title compound (0.98 g, 26%) as a white foam; $\delta_H$ (CD3OD) 0.10–0.17 (27H, m, 9×SiCH3), 0.92 (3H, d, J7.0 Hz, 17-H3), 1.19 (3H, d, J 6.3 Hz. 14-H3), 1.33–1.44 (1H, m, 12-H), 1.69–1.88 (3H, m, 9-H2 and 8-H), 2.36 (1H, dd J 13.4 and 10.6 Hz, 4-H), 2.47 (3H, s, 15-H3), 2.60 (1H, d, J 13.4 Hz, 4-H), 2.72–2.80 (2H, m, 10 and 11-H), 3.40–3.94 (8H, m, 5,7, 13, 6-H, 16-H2 and CH2Ph), 7.58 (1H, dd, J 7.8 and 4.6 Hz, 3'-H), 8.06 (1H, d, J 7.8 Hz, 40 -H), 8.65 (1H, d, J 4.6 Hz,2'-H).

b) E-6-2-[3R,4R-Dihydroxy-5S-(2S,3S-epoxy-5S-hydroxy- 4S-methylhexyl)tetrahydropyran- 2S-yl)]-(1-methyl-ethylidene))-5,6-dihydro-7H-cyclopenta[b]pyrid-7-one The above ketone (0.97 g, 1.53 mmol) and hydrochloric acid (0.4N) (9.2 ml, 3.68 mmol) in THF (45 ml) were stirred at room temperature for 2 min. Addition of saturated sodium hydrogen carbonate solution (20 ml), extraction with ethyl acetate, drying (Na2SO4), evaporation to dryness under reduced pressure, and purification by flash chromatography using 10% methanol in dichloromethane as eluent gave the title compound (0.16 g, 25%) as a white foam: $\nu_{max}$ (KBr) 3428, 2969, 2921, 1695, 1625, 1427, 1277, 1106, 1056, 1005 cm$^{-1}$; $\lambda_{max}$ (EtOH) 292.0 nm ($\epsilon_m$ 16169); $\delta_H$(CD3OD) 0.94(3H, d, J 7.1 Hz, 17-H3), 1.19 (3H, d, J 6.4 Hz, 14-H3), 1.33–1.47 ( 1H, m, 12-H), 1.62–1.81 (2H, m, 9-H2), 1.87–1.97 (1H, m, 8-H), 2.49 (3H, s, 15-H3), 2.45 (1H, dd, J 13.5 and 9.7 Hz, 4-H), 2.70–2.84 (3H, m, 4, 10 and 11-H), 3.42 (1H, dd, J 9.3 and 3.0 Hz, 6-H), 3.54 (1 H, d, J 11.8 Hz, 16-H), 3.72–3.92 (6H, m, 5, 7, 13, 16-H and CH2Ph), 7.58(1H, dd, J7.9 and 4.7 Hz, 3'-H),8.06(1H, d, J 7.9 Hz, 4'-H),8.65 (1H, d, J 4.7 Hz, 2'-H); $\delta_C$ (CD3OD) 12.3 (C-17), 19.5 (C-15), 20.4 (C-14), 30.8 (CH2Ph), 33.1 (C-9), 41.9 (C-8), 41.6 (C-4), 43.7 (C-12), 56.9 (C-10), 61.3 (C-11), 66.5 (C-16), 70.4 (C-6), 70.7 (C-7), 71.7 (C-13), 76.9 (C-5), 128.8, 131.8 (q), 136.9, 145.1 (q), 150.7, 156.3 (q), 156.8 (q), 193.7 (C-1); m/z 419 (M+, 17%); (Found M+, 417.2151. C23H31NO6 requires M, 417.2154).

EXAMPLE 15

E-6-{2-[3R,4R-Dihydroxy-5S-(2S,3S-epoxy-5S-hydroxy-4S-methylhexyl)-tetrahydropyran-2S-yl]-1-methylethylidene}6,7-dihydro-5H-cyclopenta[b]-2-methoxypyridin-5-one a) 3-Bromo-2-bromomethyl-6-methoxypyridine-3-Bromo-6-methoxy-2-methylpyridine( 11.44 g, 56.6 mmol) and N-bromo-succinimide (12.09 g, 68.0 mmol) in carbon tetrachloride (250 ml) were heated to reflux over a 150 W light bulb for 3 h. The solution was cooled to 5° C. filtered and evaporated to dryness under reduced pressure. Purification by flash chromatography using hexane/dichloromethane (5:1) as eluent gave the title compound (8.47 g, 53%) as a white solid: $\delta_H$ (CDCl3) 3.92 (3H, s, OCH3), 4.60 (2H, s, CH2Br), 6.58 (1H, d, J 8.7 Hz, 5-H), 7.66 (1H, d, J 8.7 Hz, 4-H); m/z (E.I.) 281 (M+, 67%), 200 (100%); (Found: M+, 278.8899. C7H7NOBr2 requires M, 278.8894).

b) E-6-(2-[3R-4R-Bistrimethylsilyloxy-5S-(25.3S-epoxy-5S-trimethyl-silyloxy- 4S-methylhexyl)tetra hydropyran-yl] -(1-methylethylidene))-6,7-dihydro- 5H-cyclopenta[b]-2-methoxypyridin-5-one Diisopropylamine (0.16 ml, 1.16 mmol)and t-butyl-lithium (1.7M in hexane (3.88 ml, 6.60 mmol) were added dropwise sequentially to N-methoxy-N-methyl-6,7,13-O-tris(trimethylsilyl)monamide( 3.60 g, 6.00 mmol)in THF (30 ml) maintaining the temperature below −65° C. After 1 h at −70° C. 3-bromo-2-bromomethyl-6-methoxypyridine( 8.47 g, 42 mmol) was added and the mixture heated to reflux for 60 h. The products were poured into water and extracted with ethyl acetate, dried (Na2SO4) and evaporated to dryness under reduced pressure. Removal of the excess benzyl bromide present by flash chromatography using hexane/ethyl acetate (4:1) as eluent gave a complex mixture (1.39 g). This mixture was treated with t-butyllithium (1.7M in hexane) (2.24 ml, 3.81 mmol) in THF (20 ml) at −70° C. for 2 h. Addition of water, extraction with ethyl acetate, drying (Na2SO4), evaporation to dryness under reduced pressure and purification by flash chromatography using hexane/ethyl acetate (11:2) as eluent gave a complex mixture containing the required deconjugated ketones (0.88 g). This mixture was treated with potassium t-butoxide (1.0M in THF) (1.59 ml, 1.59 mmol) in THF (10 ml) at −90° C. for 2 h. Acetic acid (0.09 ml, 1.59 mmol) then water were added. Extraction with ethyl acetate, drying (Na2SO4), evaporation to dryness under reduced pressure and purification by flash chromatography using hexane/ethyl acetate (17:3) as eluent gave the title compound (0.55 g, 14%) as a white foam; $\delta_H$ (CD3OD) 0.10–0.27 (27H, m, 9×SiCH3), 0.92 ( 3H, d, J 7.0 Hz, 17-H3), 1.20 (3H, d, J 6.3 Hz, 14-H3), 1.28–1.42 (1H, m, 12-H), 1.67–1.83 ( 3H, m, 9-H2 and 8-H), 2.36 (1H, dd, J 13.4 and 10.5 Hz, 4-H), 2.42 (3H, s, 15-H3), 2.58 (1H, d, J 13.4 Hz, 4-H), 2.72–2.82 (2H, m, 10 and 11 -H), 3.50–3.95 (8H, m, 5, 7, 13, and 16-H, 16-H2 and CH2Ph), 4.02 (3H, s, OCH3), 6.78 ( 1H, d, J 8.7 Hz, 3'-H), 7.91 (1H, d, J 8.7Hz, 4'-H); m/z 663 (M⁺, 43%), 73 (100%).; (Found: M⁺, 663.3436.C₃₃H₅₇NO₇Si requires M, 663.3443).

c) E-6-(2-[3R,4R-Dihydroxy-5S-(2S,3S-epoxy-5S-hydroxy- 4S-methyl-hexyl)tetrahydropyran- 2S-yl)]-(1-methylethylidene))-6,7-dihydro-5H-cyclopenta[b]-2-methoxypyridin-5-one The above ketone (0.55 g, 0.83 mmol) in THF (25 ml) was treated with hydrochloric acid (0.4N) (5 ml) at room temperature for 2 mins. Addition of saturated sodium hydrogen carbonate solution (15 ml), extraction with ethyl acetate, drying (Na₂SO₄) evaporation to dryness under reduced pressure, and recrystallisation from ethyl acetate and methanol gave the title compound (0.27 g, 73%) as white needles (m.p. 183.4° C.); $v_{max}$ (KBr) 3493, 2976, 2920, 2836, 1684, 1625, 1585, 1324, 1086, 1063 cm⁻¹; $\lambda_{max}$ (EtOH) 303.5 nm ) ($\epsilon_m$ 22.369) and 259.5 nm ($\epsilon_m$ 11604); $\epsilon_H$ (CD₃OD) 0.94 (3H, d,J 7.1 Hz. 17-H₃), 1.19 (3H, d, J 6.4 Hz, 14-H₃), 1.33–1.44 (1H, m, 12-H), 1.61–1.83 (2H, m, 9-H₂), 1.87–1.97 (1H, m, 8-H), 2.43 (3H, s, 15-H₃), 2.45 (1H, dd, J 13.6 and 9.6 Hz. 4-H), 2.72–2.84 (3H, m, 4, 10 and 11-H), 3.43 (1H, dd, J 9.3 and 3.0 Hz, 6-H), 3.5 (1H, d, J 11.6 Hz, 16-H), 3.67–3.94 (6H, m, 5, 7, 13, 16-H and CH₂Ph), 4.08(3H, s, OCH₃),6.78 (1H, d, J8.5 Hz, 3'-H), 7.91 (1H, d, J 8.5 Hz, 4'-H); $\delta_C$ (CD₃OD) 12.2 (C-17), 19.2 (C-14), 20.3 (C-15), 32.9 (C-9), 35.6 (C-7'), 41.6 (C-4), 41.7 (C-8), 43.6 (C-12), 56.8 (C-10), 61.3 (C-11), 66.4 (C-16), 70.3 (C-6), 70.7 (C-7), 71.6 (C-13), 76.7 (C-5), 112.0, 128.8 (q), 132.3 (q), 135.2 (q), 169.8 (q), 170.9 (q), 193.4 (C-1); m/z 447 (M⁺, 3%); (Found: M⁺· 447.2246. C₂₄H₃₃NO₇ requires M, 447.2257).

EXAMPLE 16

E-6-{2-[3R,4R-Dihydroxy-5S-(2S,3S-epoxy-5S-hydroxy-4S-methyl)-tetrahydropyran-3S-yl]-1-methylethylidene}-5,6-dihydro-7H-cyciopenta[c]-3-methoxypyridin-7-one a) 3-Bromo-6-hydroxy-4-methyl pyridine Sodium nitrite (5.44 g, 78.8 mmol) in water (14 ml) was added dropwise to 2-amino-5-bromo-4-methylpyridine (12.83 g, 68.6 mmol) in sulphuric acid (20%) (69 ml) at 0–5° C. After 1 h at 0° C. the solution was heated to reflux for 1 h. The solution was basified to pH 10 with sodium hydroxide solution (40%) and cooled to 5° C. and the precipitated product separated by filtration. Recrystallisation from ethanol gave the title compound (5.97 g, 31%) as white needles (m.p.200°–201° C.); $\delta_H$ (D₆-DMSO) 2.17 (3H, s, CH₃), 6.40 (1H, s, 3-H), 7.76 (1H, s, 6-H), 11.58 (1H, s, NH): m/z (E.I.) 189 (M⁺, 100%), 187 (M⁺, 97%); (Found: M⁺, 186.9634. C₆H₆NOBr requires M, 186.9633).

b) 3-Bromo-6-methoxy-4-methylpyridine

The above pyridine (5.95 g, 31.7 mmol), methyl iodide (6.36 g, 44.8 mmol) and silver carbonate (6.93 g, 25.1 mmol) in benzene (60 ml) were heated to 40° C. for 3 days. Filtration, evaporation to dryness under reduced pressure and purification by flash chromatography using hexane/dichloromethane (2:1) as eluent gave the title compound (4.73 g, 74%) as a white solid; $\delta_H$ (CDCl₃) 2.33 (3H, s, CH₃), 3.89 (3H, s, OCH₃), 6.64 (1H, s, 5-H), 8.18 (1 H, s, 2-H): m/z (E.I.) 203 (M⁺· 47%), 202 [(M-H)⁺, 100%], 201 (M⁺, 45%): (Found: M⁺, 199.9715. C₇H₇NOBr requires M, 199.9711 ).

c) 3-Bromo-4-bromomethyl-6-methoxypyridine

The above pyridine (4.73 g, 23.4 mmol) and N-bromosuccinimide in carbon tetrachloride (125 ml) were heated to reflux over a 150 W light bulb for 3 h. Filtration, evaporation to dryness under reduced pressure and purification by flash chromatography using hexane/ethyl acetate (19:1) as eluent gave the title compound (1.75 g, 27%) as a white solid: $\delta_H$(CDCl₃) 3.63 (3H, s, OCH₃), 4.10 (2H, s, CH₂Br, 6.36 (1H, s, 5-H), 8.25 (1H, s, 2-H): m/z (E.I.) 283 (M⁺, 20%), 93 9100%); (Found: (M-H)⁺, 277.8821. C₇H₆NOBr₂ requires M-H, 277.8816).

d) E-6-(2-[3R,4R-Bistrimethyisilyloxy-5S-(2S,3S-epoxy-5S-trimethylsilyloxy- 4S-methylhexyl)tetrahydropyran-2S-yl)]-(1-methylethylidene))- 5,6-dihydro-7H-cyclopenta[c]-3-methoxypyridin-7-one Diisopropylamine (0.16 ml, 1.16 mmol) and t-butyllithium (1.7M in hexane (3.88 ml, 6.60 mmol) were added dropwise sequentially to N-methoxy-N-methyl-6,7, 13-O-tris(trimethylsilyl)monamide( 3.60 g, 6.00 mmol) and 4-dimethylaminopyridine(catalytic amount) in THF (30 ml) maintaining the temperature below –65° C. After 1 h at –70° C., 3-bromo-4-bromomethyl-6-methoxypyridine (1.75 g, 6.22 mmol) in THF (10 ml) was added dropwise. The solution was warmed to RT over 1 h and acetic acid (0.30 ml) then added. The products were poured into water and extracted with ethyl acetate, dried (Na₂SO₄) and evaporated to dryness under reduced pressure. Removal of the excess benzyl bromide present by flash chromatography using hexane/ethyl acetate (4:1) as eluent gave a complex mixture (3.21 g). This mixture was treated with t-butyllithium (1.7M in hexane) (5.20 ml. 8.84 mmol) in THF (20 ml) at –70° C. for 2 h. Addition of water, extraction with ethyl acetate, drying (Na₂SO₄), evaporation to dryness under reduced pressure and purification by flash chromatography using hexane/ethyl acetate (4:1) as eluent gave a complex mixture containing the required deconjugated ketones (2.06 g). This mixture was treated with potassium t-butoxide (1.0 m in THF) (3.72 ml, 3.72 mmol) in THF (10 ml) at –90° C. for 2 h. Acetic acid (0.30 ml, 5.24 mmol) then water were added. Extraction with ethyl acetate, drying (Na₂SO₄), evaporation to dryness under reduced pressure and purification by flash chromatography using hexane/ethyl acetate (6:1) as eluent gave the title compound (1.29 g, 22%) as a white foam; $\delta_H$ (CD₃OD) 0.10–0.21 (27H, m, 9×SiCH₃), 0.92 (3H, d, J7.0 Hz, 17-H₃), 1.20 (3H, d, J 6.3 Hz, 14-H₃), 1.23–1.37 (2H, m, 12-H), 1.61–1.85 (3H, m, 9-H₂ and 8-H), 2.36 (1H, dd, J 13.4 and 10.5 Hz, 4-H), 2.40 (3H, s, 15-H₃), 2.58 (1H, d, J 13.4 Hz, 4-H), 2.72–2.78 (2H, m, 10 and 11-H), 3.50–3.95(8H, m, 5, 7, 13, 16-H, 16-H₂and CH₂Ph), 3.98 (3H, s, OCH₃), 6.86 (1H, s, 4'-H), 8.55 ( 3H, s, 1'-H); m/z 663 (M⁺, 3%), 73 (100%); (Found: M⁺, 663.3456. C₃₃H₅₇NO₇Si₃ requires M, 663.3443).

e) E-6-(2-[3R,4R-Dihydroxy-5S-(2S,3S-epoxy-5S-hydroxy- 4S-methylhexyl)tetrahydropyran- 2S-yl ) ]4 1-methylethylidene))-5,6-dihydro-7H-cyciopenta[c]-3-methoxypyridin-7-one The above ketone (1.29 g, 1.95 mmol) in THF (56 ml) was treated with hydrochloric acid (0.4N) (12 ml) at room temperature for 2 mins. Addition of saturated sodium hydrogen carbonate solution (25 ml), extraction with ethyl acetate, drying (Na₂SO₄) evaporation to dryness under reduced pressure, and recrystallisation from hexane, ethyl acetate and methanol gave the title compound (0.54 g, 80%) as white needles (m.p. 167°–8° C.); $v_{max}$ (KBr) 3427, 2965, 2937, 2836, 1684, 1624, b1607, 1317, 1271 cm⁻¹; $\lambda_{max}$ (EtOH) 297 nm ($\epsilon_m$ 26201) and 227 nm ($\epsilon_m$ 12386); $\lambda_H$ (CD₃OD) 0.94 (3H, d, J 7.1 Hz, 17-H₃), 1.19(3H, d, J 6.4 Hz, 14-H₃), 1.33–1.44 (1H, m, 12-H), 1.61–1.83 (2H, m, 9-H₂), 1.87–1.97 (1H, m, 8-H), 2.43 (2H, s, 15-H₃), 2.45 (1H, dd, J 13.6 and 9.6 Hz, 4-H), 2.72–2.84 (3H, m, 4, 10 and 11-H), 3.41 (1H, dd, J 9.3 and 3.0 Hz, 6-H), 3.54 (1H, d, J 11.6 Hz, 16-H), 3.67–3.94 (6H, m, 5, 7, 13, 16-H and C$H_2$Ph), 3.99 (3H, s, OC$H_3$), 6.88 (1H, s, 4'-H), 8.56 ( 1H, s, 1'-H); δ$_C$ (CD$_3$OD) 12.2 (C-17), 19.2 (C-14), 20.3 (C-15), 32.7 (C-9), 32.7 (C-7'), 41.4 (C-8), 41.7 (C-4), 43.6 (C-12), 54.8 (OCH$_3$), 56.8 (C-10), 61.3 (C-11), 66.4 (C-16), 70.3 (C-6), 70.7 (C-7), 71.3 (C-13), 76.5 (C-5), 107.4, 131.7 (q), 132.5 (q), 145.7 (q), 160.2 (q), 168.3 (q), 193.4 (C-1); m/z 447 (M$^+$, 2%); (Found: C, 64.1; H, 7.41; N, 3.25. C$_{24}$H$_{33}$NO$_7$ requires C, 64.4: H, 7.43; N, 3.25).

EXAMPLE 17

E-2-(2-[3R,4R-Dihydroxy-5S-(2S,3S-epoxy-5S-hydroxy-4S-methylhexyl)-tetrahydropyran-2S-yl)]-(1-methylethylidene))-5-dimethylaminoindan-1-one.

a) 2-Bromo-5-dimethylaminobenzene acid methyl ester 2,4,4,6-Tetrabromo-2,5-cyclohexanedione( 8.19 g, 20.0 mmol) was added portionwise to 3-dimethylaminobenzoic acid methyl ester (3.58 g, 20.0 mmol) in dichloromethane (125 ml) at −20° C. over 1 h. The solution was warmed to room temperature over 0.5 h and stirred for a further 2 h at that temperature. The solution was washed with 2.5N sodium hydroxide solution (3×150 ml), dried (Na$_2$SO$_4$) and evaporated to dryness under reduced pressure. Purification by flash chromatography using dichloromethane/hexane (3:1) as eluent gave the title compound (4.71 g, 91% ) as a pale yellow liquid; δ$_H$ (CDCl$_3$) 2.96 ( 6H, s, N(C$H_3$)$_2$), 3.93 (3H, s, OC$H_3$), 6.68 (1H, dd, J 8.9 and 3.2 Hz, 3-H), 7.08 ( 1H, d, J 3.2 Hz, 5-H), 7.43 (1H, d, J 8.9 Hz, 2-H); m/z (E.I.) 261 (M$^+$, 42%), 259 (M$^+$, 41%), 83 (100%); (Found: M$^+$, 257.0056. C$_{10}$H$_{12}$NO$_2$Br requires M, 257.0051).

b) 1-Bromo-4-dimethylamino-2-hydroxymethylbenzene

The above ester (4.25 g, 16.4 mmol) in THF (40 ml) was treated dropwise with diisoburylaluminium hydride (1.0M in toluene) (36.1 ml, 36.1 mmol) at −70° C. After 2 h at −70° C. saturated aqueous sodium sulphate solution (40 ml) and methanol (40 ml) were added. After 0.5 h at room temperature dichloromethane (100 ml) was added the precipitated solids removed by filtration. Drying (Na$_2$SO$_4$), evaporation to dryness under reduced pressure and recrystallisation from ethyl acetate/hexane gave the title compound (2.20 g, 58%) as white needles; δ$_H$ (CDCl$_3$) 2.00 (1H, t, J 4.1 Hz, OH), 2.95 (614, s, N(CH$_3$)$_2$), 4.69 (2H, d, J 4.1 Hz, C$H_2$OH), 6.52 (1H, dd, J 3.1 and 8.9 Hz, 5-H), 6.82 (1H, d, J 3.1 Hz, 3-H), 17.34 (1H, d, J 8.9 Hz, 6-H); m/z (E.I.) 231 (M$^+$, 15%), 229 (M$^{30}$, 23%); (Found: M$^+$, 229.0102. C$_9$H$_{12}$NOBr requires M, 229.0102).

c) 1-Bromo-2-bromomethyl-4-dimethylaminobenzene

Bromine (3.45g, 21.6 mmol) in dichloromethane (10 ml) was added dropwise to the above alcohol (4.53 g, 19.61 mmol) and triphenylphosphine (5.66 g, 21.6 mmol) in dichloromethane (50 ml) at −30° C. After 1 h at −20° C., excess 10% aqueous sodium carbonate solution was added. Extraction with ethyl acetate, drying (MgSO$_4$), evaporation to dryness under reduced pressure and purification by flash chromatography using hexane/ethyl acetate (6:1) as eluent gave the title compound (2.80 g, 49%) as a white solid; δ$_H$(CDCl$_3$) 2.94 (6H, s, N(CH$_3$)$_2$), 4.56 (2H, s, CH$_2$Br), 6.52 ( 1H, dd, J 8.9 and 3.1 Hz, 5-H), 6.74 (1H, d, J 3.1 Hz, 3-H), 7.35 (1H, d, J 8.9 Hz, 6-H): m/z (E.I.) 295 (M$^{30}$, 28%), 293 (M$^+$, 51%), 291 (M$^+$, 29%), 212 (100%); (Found: M$^+$, 290.9523. C$_9$H$_{11}$NBr$_2$ requires M, 290.9258).

d) E-2-(2-[3R,4R-Bistrimethylsilyloxy-5S-(2S,3S-epoxy-5S-trimethylsilyloxy- 4S-methylhexyl)tetrahydropyran-3S-yl]-(1-methylethylidene))-5-dimethylaminoindan-1-one Diisopropylamine (0.16 ml, 1.16 mmol) and t-butyllithium (1.7M in hexane (3.88 ml, 6.60 mmol) were added dropwise sequentially to N-methoxy-N-methyl- 6,7,13-O-tris(trimethylsilyl)monamide (3.60 g, 6.00 mmol) and 4-dimethylaminopyridine(catalytic amount) in THF (30 ml) maintaining the temperature below −65° C. After 1 h at −70° C. 1-bromo-2-bromomethyl- 4dimethylaminobenzene( 2.80 g, 9.52 mmol) in THF (10 ml) was added dropwise. The solution was warmed to RT over 1 h and acetic acid (0.30 ml) then added. The products were poured into water and extracted with ethyl acetate, dried (Na$_2$SO$_4$) and evaporated to dryness under reduced pressure. Removal of the excess benzyl bromide present by flash chromatography using hexane/ethyl acetate (2:1) as eluent gave a complex mixture (2.07 g). This mixture was treated with t-buryllithium (1.7 M in hexane) (3.29 ml, 5.59 mmol) in THF (20 ml) at −70° C. for 2 h. Addition of water, extraction with ethyl acetate, drying (Na$_2$SO$_4$), evaporation to dryness under reduced pressure and purification by flash chromatography using hexane/ethyl acetate (3:1) as eluent gave a complex mixture containing the required deconjugated ketones (0.89 g). This mixture was treated with potassium t-butoxide (1.0 m in THF) (1.60 ml, 1.60 mmol) in THF (10 ml) at −90° C. for 2 h. Acetic acid (0.30 ml), 5.24 mmol) then water were added. Extraction with ethyl acetate, drying (Na$_2$SO$_4$), evaporation to dryness under reduced pressure and purification by flash chromatography using hexane/ethyl acetate (4:1) as eluent gave the title compound (0.52 g, 12%) as a white foam: δ$_H$ (CD$_3$OD) 0.10–0.21 (27H, m, 9×SiCH$_3$), 0.92 ( 3H, d, J 7.0 Hz, 117-H$_3$), 1.20 (3H, d, J 6.3 Hz, 14-H$_3$), 1.28–1.43 (2H, m, 12-H), 1.63–1.87 (3H, m, 9H$_2$ and 8-H), 2.3 (1H, dd, J 13.4 and 10.5 Hz, 4-H), 2.40 (3H, s, 15-H$_3$), 2.5 (1H, d, J 13.4 Hz, 4-Ht), 2.72–2.78 (2H, m, 10 and 11-H), 3.09 (6H, s, N(C$H_3$), 3.50–3.95 (8H, m, 5, 7, 13.6-H, 16-H$_2$ and CH$_2$Ph), 6.65 (1H, d, J 2.1 Hz, 4'-H), 6.75 (1H, dd, J 8.8 and 2.1 Hz, 6'-H), 17.57 (1H, d, J 8.8 Hz, 17'-H); m/z675 (M$^+$, 4%), 173 (100%); (Found: M$^+$, 675.3805. C$_{35}$H$_{61}$NO$_6$Si$_3$ requires M, 675.3807).

e) E-(2-[3R,4R-Dihydroxy-5S-(2S,3S-epoxy-5S-hydroxy-4S-methylhexyl)tetra-hydropyran- 2S-yl]-(1-methylethylidene))-5-dimethylaminoindan-1-one The above ketone (0.51 g, 0.77 mmol) in THF (25 ml) was treated with hydrochloric acid (0.4N ) (5 ml) at room temperature for 2 mins. Addition of saturated sodium hydrogen carbonate solution (20 ml), extraction with ethyl acetate, drying (Na$_2$SO$_4$) evaporation to dryness under reduced pressure, and purification by flash chromatography using 7% methanol in dichloromethane as eluent gave the title compound (0.31 g, 89%) as a yellow foam: ν$_{max}$ (KBr) 3414, 2968, 2901, 1664, 1619, 1594, 1369, 1301 cm$^{-1}$; λ$_{max}$ (EtOH) 368 nm (ε$_m$ 26,378), 275 nm (ε$_m$ 11,836) and 265 nm (ε$_m$ 12,197); δ$_H$ (CD$_3$OD) 0.90 (3H, d, J 7.1 Hz, 17 -H$_3$), 1.19 (3H, d, J 6.4 Hz, 14-H$_3$), 1.33–1.44 (1H, m, 12-H), 1.61–1.83 (2H, m, 9-H$_2$), 1.87–1.97 (1H, m, 8-H), 2.40 (3H, s, 15-H$_3$), 2.40 (1H, dd, J 13.6 and 9.6 Hz, 4-H), 2.67–2.81 (3H, m, 4, 10 and 11-H), 3.08 (6H, s, N(CH$_3$)$_2$), 3.41 (1H, dd, J 9.3 and 3.0 Hz, 6-H), 3.54–3.69 (3H, m, 16H, and 3'-H$_2$),3.73–3.94(4H, m, 5, 7, 13, 16-H), 6.65 (1H, d, J 2.3 Hz, 4'-H), 6.74 (1H, dd, J2.3 and 8.8 Hz, 6'-H), 7.56 ( 1H, d, J 8.8 Hz, 7'-H); m/z 459 (M$^+$, 8%); (Found: M$^+$, 459.2619. C$_{26}$H$_{37}$NO$_6$ requires M, 459.2621).

EXAMPLE 18

E-6-(2-[3R-4R-Dihydroxy-5S(2S,3S-epoxy-5S-hydroxy-4S-methylhexyl)-tetrahydro-pyran-2S-yl)]-(1-methylethylidene))-5,6-dihydro-7H-cyclopenta-[c]-3-(morpholin-4-yl)-pyridin-7-one a) 2.5-Dibromo-4-acetoxymethylpyridine 2.5-Dibromo-4-methylpyridine( 26.06 g, 103.8 mmol) and N-bromosuccinimide (27.72 g, 155.7 mmol) in carbon tetrachloride (500 ml) were heated to reflux over a 150 W light bulb for 2 h. Cooling to 5° C., filtration and evaporation to dryness under reduced pressure gave the crude brominated products which were treated with potassium acetate (66.0 g, 673 mmol) and 18-crown-6 (3.00 g, 11.4 mmol) in acetonitrile (500 ml) at room temperature for 40 h. Filtration and evaporation of the filtrate to dryness gave the crude products which were dissolved in ethyl acetate, washed with saturated aqueous potassium bromide solution, the organic phase dried ($Na_2SO_4$) and evaporated to dryness under reduced pressure with purification by flash chromatography using hexane/ethyl acetate (6:1) as eluent giving the title compound (6.56 g. 19%) as a white solid: $\delta_H$ ($CDCl_3$), 2.22 (3H, s, $CH_3$), 5.12 ( 2H, s, $CH_2OAc$), 17.50 (1H, s, 3-H), 18.45 (1H, s, 6-H); m/z (E.I.) 308 ($MH^+$, 3%), 230 (100%): (Found: $M^+$, 307.8926. $C_8H_8NO_2Br$ requires M. 307.89221.

b) 2.5-Dibromo-4-hydroxymethylpyridine

The above pyridine (6.56 g, 20.3 mmol) in methanol (400 ml) and concentrated sulphuric acid (2 ml) was heated to reflux for 16 h. Neutralisation with 10% aqueous sodium carbonate solution extraction with ethyl acetate, drying ($Na_2SO_4$), evaporated to dryness under reduced pressure and recrystallisation from ethyl acetate/hexane gave the title compound (4.88 g, 90%) as white needles; $\delta_H$ ($CDCl_3$) 2.26 ( 1H, br. s, $OH$), 4.74 (2H, s, $CH_2$), 7.73 (1H, s, 3-H), 18.39 (1H, s, 6-H): m/z (E.I.) 269 ($M^+$, 22%), 267 ($M^{+,}$ 45%), 2.65 ($M^+$, 23%), 186 (100%); (Found: M, 264.8745. $C_6H_5NOBr_2$ requires M, 264.8738).

c) 3-Bromo-4-hydroxymethyl-6-(morpholin-4-yl)pyridine

The above bromopyridine (1.21 g, 4.53 mmol) in morpholine (5 ml) was heated to 90° C. for 3 h 10% Aqueous sodium carbonate solution (15 ml) was added, extraction with ethyl acetate, drying ($Na_2SO_4$), evaporation to dryness under reduced pressure and purification by flash chromatography using ethyl acetate/hexane (2:1) as eluent gave the title compound (1.00 g. 81%) as a white solid: $\delta_H$ ($CD_3OD$) 3.45–3.49 (4H, m, $2 \times NCH_2$), 3.75–3.80 (4H, m, $2 \times OCH_2$), 4.56 ( 2H, s, $CH_2OH$), 6.98 (1H, s, 5-H), 8.08 (1H, s, 2-H): m/z (E.I.) 274 ($M^+$, 47%), 272 ($M^+$, 50%), 187 (100%); (Found: $M^+$, 272.0164. $C_{10}H_{13}N_2O_2Br$ requires M, 272.0160).

d) 3-Bromo-4-bromomethyl-6-(morpholin-4-yl)pyridine

Bromine (0.64 g, 0.21 ml, 4.00 mmol) in dichloromethane (3 ml) was added dropwise to the above alcohol (0.99 g, 3.63 mmol) and triphenylphosphine (1.05 g, 4.00 mmol) in dichloromethane (25 ml) at −40° C. After 1 h at +40° C. the solution was warmed to RT over 1 h. Neutralisation with 10% aqueous sodium carbonate solution, extraction with ethyl acetate, drying ($Na_2SO_4$), evaporation to dryness under reduced pressure and purification by flash chromatography using hexane/ethyl acetate (4:1) as eluent gave the title compound (1.04 g, 85%) as a white solid; $\delta_H$ ($CDCl_3$) 3.47–3.51 (4H, m, $2 \times NCH_2$), 3.79–3.83 (4H, m, $2 \times OCH_2$), 4.42 (2H, s, $CH_2Br$), 6.70 (1H, s, 5'-H), 8.24 (1H, s. 2'-H); m/z (E.I.) 336 ($M^+$, 22%), 91 (100%): (Found: $M^+$, 333.9316. $C_{10}H_{12}N_2OBr_2$ requires M, 333.9316).

e]E-6-(−(2-[3R,4R-Bistrimethylsilyloxy-5S-(2S,3S-epoxy-5S-trimethylsilyloxy-4S-methylhexyl)tetrahydropyran-2S-yl]-(1-methylethylidene))-5,6-dihydro-7H-cyclopenta[c]-3-(morpholin-4-yl)-pyridin-7-one Diisopropylamine (0.08 ml, 0.58 mmol) and t-butyllithium (1.7M in hexane (1.95 ml, 3.30 mmol) were added dropwise sequentially to N-methoxy-N-methyl-6,7,13-O-tris(trimethylsilyl)monamide (1.81 g, 3.00 mmol) and 4-dimethylaminopyridine (catalytic amount) in THF (30 ml) maintaining the temperature below −65° C. After 1 h at −70° C. 3-bromo- 4-bromomethyl- 3-(morpholin-4-yl)pyridine (1.04 g, 3.09 mmol) in THF (10 ml) was added dropwise. The solution was warmed to RT over 1 h and acetic acid (0.30 ml) then added. The products were poured into water and extracted with ethyl acetate, dried ($Na_2SO_4$) and evaporated to dryness under reduced pressure. Removal of the excess benzyl bromide present by flash chromatography using hexane/ethyl acetate (1:1) as eluent gave a complex mixture (1.73 g). This mixture was treated with t-butyllithium (1.7$M$ in hexane) (2.61 ml, 4.43 mmol) in THF (20 ml) at −70° C. for 2 h. Addition of water, extraction with ethyl acetate, drying ($Na_2SO_4$), evaporation to dryness under reduced pressure and purification by flash chromatography using hexane/ethyl acetate (1:1) as eluent gave a complex mixture containing the required deconjugated ketones (1.08 g). This mixture was treated with potassium t-butoxide (1.0 m in THF) (1.86 ml, 1.86 mmol) in THF (10 ml) at −90° C. for 2 h. Acetic acid (0.2 ml, 3.72 mmol) then water were added. Extraction with ethyl acetate, drying ($Na_2SO_4$), evaporation to dryness under reduced pressure and purification by flash chromatography using hexane/ethyl acetate (2:1) as eluent gave the title compound (1.85 g, 40%) as a white foam; $\delta_H$ ($CD_3OD$) 0.10–0.21 (27H, m, $9 \times SiCH_3$), 0.92 (3H, d, J 7.0 Hz, 17-$H_3$), 1.20 (3H, d, J 6.3 Hz, 14-$H_3$), 1.28–1.43 ( 2H, m, 12-H), 1.63–1.89 (3H, m, 9-$H_2$ and 8-H), 2.33 (1H, dd, J 13.4 and 10.5 Hz, 4-H), 2.39 (3H, s, 15-$H_3$), 2.56 (1H, d, J 13.4 Hz, 4-H), 2.72–2.78 (2H, m, 10 and 11-H), 350–3.95 (16H, m, 5, 6, 7, 13, 5'-$H_2$, 16-$H_2$, $2 \times OCH_2$ and $2 \times NCH_2$), 6.77 (1H, s, 4',H), 8.52 (3H, s, 1'-H); m/z 718 ($M^+$, 48%), 73 (100%); (Found: $M^+$, 718.3879. $C_{34}H_{62}N_2O_7Si_3$ requires M, 718.3865).

f) E-6-((2-[3R,4R-Dihydroxy-5S-(2S,3S-epoxy-5S-hydroxy- 4S-methylhexyl)-tetrahydropyran- 2S-yl]-(1-methylethylidene))-5,6-dihydro-7H-cyciopenta[c]- 3-(morpholin-4-yl)-pyridin-7-one The above ketone (0.85 g, 1.18 mmol)in THF (35 ml) was treated with hydrochloric acid (0.4N) (7 ml) at room temperature for 2 mins. Addition of saturated sodium hydrogen carbonate solution (15 ml), extraction with ethyl acetate, drying ($Na_2SO_4$) evaporation to dryness under reduced pressure, and recrystallisation from ethyl acetate and methanol gave the title compound (0.48 g, 80%) as yellow needles (m.p. 185.6° C.); $\nu_{max}$ (KBr) 3372, 2965, 2890, 1675, 1624, 1601, 1438, 1295, 1245 $cm^{-1}$; $\lambda_{max}$ (EtOH) 347.5 nm ($\epsilon_m$ 22,361) and 314 nm ($\epsilon_m$ 13,634); $\delta_H$ ($CD_3OD$) 0.94 (3H, d, J 7.1 Hz, 17-$H_3$), 1.19 ( 3H, d, J 6.4 Hz, 14-$H_3$), 1.33–1.44(1H, m, 12-H), 1.61–1.83(2H, m, 9-$H_2$), 1.87–1.97( 1H, m, 8-H), 2.41 (2H, s, 15-$H_3$), 2.46 (1H, dd, J 13.6 and 9.6 Hz, 4-H), 2.72–2.84 ( 3H, m, 4, 10 and 11-H), 3.40 (1H, dd, J 9.3 and 3.0 Hz, 6-H), 3.51–3.96 (15H, m, 5, 7, 13-H, 16-$H_2$, 5'-$H_2$, $2 \times OCH_2$ and $2 \times NCH_2$), 6.77 (1H, s, 4'-H), 18.62 ( 1H, s, 1'-H); $\delta_C$ ($D_6DMSO$) 11.6 (C-17), 17.9 (C-15), 20.0 (C-14), 31.6 (C-9), 40.3 (C-12), 40.6 (C-4), 41.8 (C-8), 44.8(N($CH_2$)),54.6(C-10),59.2(C-11), 64.9(O($CH_2$)),65.8(C-16),67.7 (C-6), 68.6 (C-7), 69.4 (C-13), 75.4 (C-5), 101.2, 126.6(q), 131.4 (q), 145.4, 149.1(q), 157.3(q), 160.9(q), 190.5 (C-1); m/z (E.I.) 501 ($M^+$, 10%), 289 (100%); (Found: $M^+$, 502.7676. $C_{27}H_{38}N_2O_7$ requires M, 502.2679).

EXAMPLE 19

E-2-{2-[3R-4R-Dihydroxy-5S-(2S,3S-epoxy-5S-hydroxy-4S-methylhexyl)-tetrahydropyran-2S-yl]-1-methylethylidene}-5-(methoxycarbonypentyloxyindan-1-one)

The product from Example 12c (0.5 g, 1.15 mmol) was dissolved in THF (5 ml) and added to a suspension of sodium hydride (43 mg, 1.04 mmol) in THF (3 ml). The mixture was stirred under an atmosphere of argon for 10 mins. Methyl 6-iodohexanoate (0.3 g, 1.15 mmol) in THF (3 ml) was added followed by DMF (5 ml) and 15-crown-5 (0.1 g, 0.58 mmol). The resulting solution was stirred for 48 hours. The products were poured into water. Extraction with ethyl acetate, drying over anhydrous magnesium sulphate and evaporation of solvent yielded unreacted starting material (0.1 g). The aqueous phase was acidified to pH 5 and the products extracted with ethyl acetate. The organic phases were combined, washed with water, dried over anhydrous magnesium sulphate and evaporated. The crude product was purified by flash chromatography eluting with 5% methanol in dichloromethane to afford the title compound as a white solid (250 mg, 39%); $v_{max}$ (KBr) 3422, 2924, 1735, 1681, 1623, 1464, 1333, 1361 and 1103 cm$^{-1}$; $\lambda_{max}$ (EtOH) 309.5 nm ($\epsilon_m$ 22,954), 239.5 nm ($\epsilon_m$ 7,265) and 203.5 nm ($\epsilon_m$ 11,499); $\delta_H$ (CD$_3$OD) 0.96 (3H, d, J 7.1 Hz, 17-H$_3$), 1.2 (3H, d, J 6.5 Hz, 14-H$_3$), 1.29–2.0 (10H, m, 9H$_2$, 8, 12-H and CH$_2$), 2.37 (2H, t, J 7.3 Hz, CH$_2$), 2.42 (3H, s, 15-H$_3$), 2.5 (1H, d, J 9.7 Hz, 4-H), 2.64–2.85 (3H, m, 10, 4 and 11-H), 3.41 (1H, dd, J 3.2 and 9.2 Hz, 6-H), 3.55 (1H, d, J 11.6 Hz, 16-H), 3.63(3H, s, OCH$_3$), 3.69–3.92(6H, m, 7, 5, 13, 16 and CH$_2$-Ph), 4.08 (2H, t, J 6.3 Hz. CH$_2$), 6.91 (1H, dd, J 2.2 and 8.6 Hz, Ar-H), 6.99 (1H, d, Ar-H), 7.61 (1H, d, J 8.6 Hz, Ar-H); m/z (MH$^+$) 561.

EXAMPLE 20

E-2-{2-[3R,4R-Dihydroxy-5S-(2S,3S-epoxy-5S-hydroxy-4S-methylhexl)tetrahydropyran-2S-yl]-1-methylethylidene}-5-(5-carboxypentyloxyindan-1-one)

The methyl ester from Example 19 (10 mg, 0.018 mmol) was stirred in pH 7 buffer Na$_2$HPO$_4$ (9 ml) and acetone (1 ml). Subtilisin Carlsburg (6 mg) was added and the resulting suspension was stirred for 48 hours. The solvent was removed by freeze drying. The residue was treated with ethanol (25 ml) and filtered. The filtrate was evaporated and the resulting solid was dissolved in water and acidified to pH 3. The products were extracted with ethyl acetate and the combined organic extracts were washed with water, dried with anhydrous magnesium sulphate, and the solvent removed to give the desired product as a white solid (7.3 mg, 75%); $\delta_H$ (CD$_3$OD)0.95 (3H, d, J7.1 Hz, 17-H$_3$), 1.21 (3H, d, J 6.5 Hz, 14-H$_3$), 1.29–2.0 (10H, m, 9-H$_2$, 8 and 12-H and CH$_2$), 2.31 (2H, t, J 7.3 Hz. CH$_2$), 2.42 (3H, s, 15-H$_3$), 2.48(1H, d, J9.7 Hz, 4-H), 2.69–2.88(3H, m, 4, 10 and 11-H),3.41 (1H, dd, J 3.0 Hz and 9.2 Hz, 6-H), 3.53 (1H, d, J 11.5 Hz, 16-H), 3.69–3.93 (6H, m, 5, 7, 13, 16 and CH$_2$Ph), 4.08 (2H, t, J 6.4 Hz, CH$_2$), 6.92 (1H, dd, J 2.2 and 8.5 Hz, Ar-H), 7.0 (1H, d, Ar-H), 7.63 (1H, d, J 8.5 Hz, Ar-H).

Biological Data

The antibacterial activity of compounds of the present invention, as exemplified by Examples 1 to 20, was assessed against a range of organisms selected from H. influenzae Q1; B. Catarrhalis 1502; S. pyogenes CN10; S. pneumoniae Pu7; and S. aureus Oxford, in a conventional microbiological assay, using serial dilutions in nutrient agar with 5% chocolated horse blood. The MICs were determined after incubation for 18 h at 37°. Values in the range 0.06 to 64 µgml$^{-1}$ were observed.

The antibacterial activity of compounds of the instant invention against the Legionella organisms may be assayed in the following manner: Culture is thawed from frozen skim milk stocks and streaked onto supplemented buffered charcoal yeast extract agar (BCYEα, Oxoid). Three days later, colonies are suspended in tissue culture medium (TCM= Eagle's Minimal Essential Midium+Earles' salts supplemented with 10% foetal calf serum, 2 mM L-glutamine and 1% non-essential amino acids) to MacFarland's barium sulphate opacity standard 0.5. The suspension is further diluted 1:100 in TCM to yield a final inoculum of 4.83×10$^6$ cfu/ml. Human foetal lung fibroblast (MRC-5) cells are then inoculated. These cells are previously grown to 80% confluency in 6-well plates, the medium removed and the monolayers washed twice with Dulbecco's PBS. Sixteen hours after inoculation(time 0 h), the medium is removed and the inoculated monolayers washed twice to remove any adherent, non-intracellular, organisms. Test compound, prepared to the required concentrations in TCM, is added to the cells. At 0, 3, 12, 24, 36, 48 and 72 h after the dose, the medium is removed from one well/treatment, and the monolayers washed twice. Sterile distilled water is added and left for 30 min to lyse the cells. After vigorous trituration, the lysate is serially diluted in Mueller Hinton brother and plated onto BYCEα and 5% horse blood agars. Colonies of L.pneumophila are counted after 72 h incubation at 37° C. In addition and by way of confirmation, the stability of the compounds in TCM may be examined over a 72 h period. A solutions of 2 µg/ml of each of the compounds is prepared in TCM and incubated at 37° C. or 4° C. and aliquots removed at intervals. The test compound and erythromycin are assayed against Bacillus subtilis ATCC 6633 and Sarcina lutea NCTC 8340, respectively, using standards prepared in TCM.

I claim:

1. A compound of formula (I):

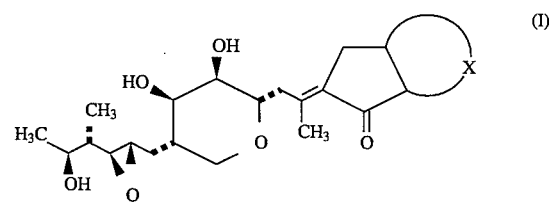

in which X is selected from the group consisting of: benzene, naphthalene, pyridine and furan, and is fused to the cyclopentanone ring at the 2:3 position, said group being optionally substituted with one or two substituents selected from: hydroxy, (C$_{1-6}$)alkoxy, (C$_{1-6}$)alkylthio, (C$_{1-6}$)alkylsulphinyl, (C$_{1-6}$)alkylsulphonyl, di-(C$_{1-6}$)alkylamino, N-morpholinyl, (C$_{1-6}$)alkoxycarbonyl and carboxy.

2. A compound as claimed in claim 1 in which the moiety:

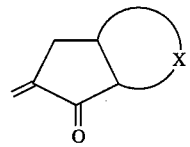

is

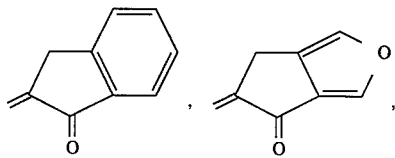

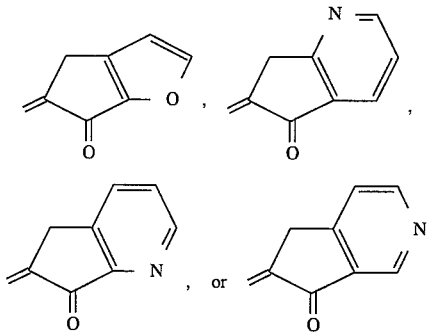

said moiety being optionally substituted with one or two substituents selected from: hydroxy, $(C_{1-6})$alkoxy, $(C_{1-6})$alkylthio, $(C_{1-6})$alkylsulphinyl, $(C_{1-6})$alkylsulphonyl, di-$(C_{1-6})$alkylamino, N-morpholinyl, $(C_{1-6})$alkoxycarbonyl and carboxy.

3. A compound of claim 1 selected from:

E-2-(2-[3R,4R-Dihydroxy-5S-(2S,3S-epoxy-5S-hydroxy-4S-methylhexyl)tetrahydropyran-2S-yl)]-(1-methylethylidene))indan-1-one;

E-2-(2-[3R,4R-Dihydroxy-5S-(2S,3S-epoxy-5S-hydroxy-4S-methylhexyl)tetrahydropyran-2S-yl)]-(1-methylethylidene))5-methoxyindan-1-one;

E-2-(2-[3R,4R-Dihydroxy-5S-(2S,3S-epoxy-5S-hydroxy-4S-methylhexyl)tetrahydropyran-2S-yl)]-(1-methylethylidene))-7-methylindan-1-one;

E-2-(2-[3R,4R-Dihydroxy-5S-(2S,3S-epoxy-5S-hydroxy-4S-methylhexyl)tetrahydropyran-2S-yl)]-(1-methylethylidene))-7-methoxyindan-1-one;

E-5-(2-[3R,4R-Dihydroxy-5S-(2S,3S-epoxy-5S-hydroxy-4S-methylhexyl)tetrahydropyran-2S-yl]-(1-methylethylidene))-5,6-dihydro-4H-cyclopenta[c]furan-4-one;

E-5-(2-[3R,4R-Dihydroxy-5-(2S,3S-epoxy-5S-hydroxy-4S-methylhexyl)tetrahydropyran- 2S-yl]-1-methylethylidene))-5,6-dihydro-4H-cyclopenta[b]furan-4-one;

E-2-(2-[3R,4R-Dihydroxy-5S-(2S,3S-epoxy-5S-hydroxy-4S-methylhexyl)tetrahydropyran- 2S-yl)]-(1-methylethylidene))-5-methoxy-7-methylindan-1-one;

E-5-(2-[3R,4R-Dihydroxy-5-(2S,3S-epoxy-5S-hydroxy-4S-methylhexyl)tetrahydropyran- 2S-yl]-1-methylethylidene))-5-methylthioindan-1-one;

E-5-(2-[3R,4R-Dihydroxy-5-(2S,3S-epoxy-5S-hydroxy-4S-methylhexyl)tetrahydropyran- 2S-yl]-1-methylethylidene))-5-methylsulphinylindan-1-one;

E-5-(2-[3R,4R-Dihydroxy-5-(2S,3S-epoxy-5S-hydroxy-4S-methylhexyl)tetrahydropyran-2S-yl]-1-methylethylidene))-5-methylsulphonylindan-1-one;

E-2-(2-[3R,4R-Dihydroxy-5S-(2S,3S-epoxy-5S-hydroxy-4-S-methylhexyl)tetrahydropyran- 2S-yl)]-(1-methylethylidene))-6-methoxyindan-1-one; and E-2-(2-[3R,4R-Dihydroxy-5S-(2S,3S-epoxy-5S-hydroxy-4S-methylhexyl)tetrahydropyran- 2S-yl)]-(1-methyl-ethylidene))-5-hydroxyindan-1-one;

E-2-(2-[3R,4R-Dihydroxy-5S-(2S,3S-epoxy-5S-hydroxy-4S-methylhexyl)tetrahydropyran- 2S-yl)]-(1-methylethylidene))-6-hydroxyindan-1-one;

E-6-(2-[3R,4R-Dihydroxy-5S(2S,3S-epoxy-5S-hydroxy-4S-methylhexyl)tetrahydropyran- 2S-yl)]-(1-methylethylidene))-5,6-dihydro-7H-cyclopenta-[b]pyridin-7-one;

E-6-{2-[3R,4R-Dihydroxy-5S-(2S,3S-epoxy- 5S-hydroxy-4S-methylhexyl)tetrahydropyran- 2S-yl]-1-methylethylidene}6,7-dihydro-5H-cyclopenta[b]-2-methoxypyridin-5-one;

E-6-{2-[3R,4R-Dihydroxy-5S-(2S,3S-epoxy-5S-hydroxy-4S-methylhexyl)tetrahydropyran- 3S-yl]-1-methylethylidene}-5,6-dihydro-7H-cyclopenta[c]-3-methoxypyridin-7-one;

E-2-(2-[3R,4R-Dihydroxy-5S-(2S,3S-epoxy-5S-hydroxy-4S-methylhexyl)tetrahydropyran- 2S-yl)]-(1-methylethylidene))-5-dimethylaminoindan-1-one;

E-6-(2-[3R,4R-Dihydroxy-5S(2S,3S-epoxy-5S-hydroxy-4S-methylhexyl)tetrahydropyran- 2S-yl)]-(1-methylethylidene))-5,6-dihydro-7H-cyclopenta-[c]-3-(morpholin-4-yl)-pyridin-7-one;

E-2-{2-[3R,4R-Dihydroxy-5S-(2S,3S-epoxy- 5S-hydroxy-4S-methylhexyl )tetrahydropyran- 2S-yl]-1-methylethylidene}-5-(methoxycarbonylpentyloxyindan-1-one); and E-2-{2-[3R,4R-Dihydroxy-5S-(2S,3S-epoxy- 5S-hydroxy-4S-methylhexyl)tetrahydropyran- 2S-yl]-1-methylethylidene}-5-(5-carboxypentyloxyindan-1-one).

4. A pharmaceutical composition comprising a compound of formula (I) as defined in claim 1 and a pharmaceutically acceptable carrier or excipient.

5. A method of treatment of bacterial and mycoplasmal infections in human and non-human animals, which comprises the administration to a human or non-human animal in need of such treatment, an effective amount of a compound according to claim 1.

* * * * *